(12) United States Patent
Aghassian et al.

(10) Patent No.: US 8,473,066 B2
(45) Date of Patent: Jun. 25, 2013

(54) EXTERNAL CHARGER FOR A MEDICAL IMPLANTABLE DEVICE USING FIELD SENSING COILS TO IMPROVE COUPLING

(75) Inventors: Daniel Aghassian, Glendale, CA (US); Lev Freidin, Simi Valley, CA (US); Joey Chen, Valencia, CA (US)

(73) Assignee: Boston Scientific Neuromodulation Company, Valencia, CA (US)

( * ) Notice: Subject to any disclaimer, the term of this patent is extended or adjusted under 35 U.S.C. 154(b) by 471 days.

(21) Appl. No.: 12/498,049

(22) Filed: Jul. 6, 2009

(65) Prior Publication Data
US 2011/0004278 A1   Jan. 6, 2011

(51) Int. Cl.
*A61N 1/00*   (2006.01)
(52) U.S. Cl.
USPC .................. 607/61; 607/30; 607/32; 607/33
(58) Field of Classification Search
USPC .......................... 607/30, 32–33, 61
See application file for complete search history.

(56) References Cited

U.S. PATENT DOCUMENTS

| | | | |
|---|---|---|---|
| 5,314,453 A | 5/1994 | Jeutter | |
| 5,749,909 A | 5/1998 | Schroeppel et al. | |
| 6,553,263 B1 | 4/2003 | Meadows et al. | |
| 2003/0114899 A1* | 6/2003 | Woods et al. | 607/60 |
| 2007/0060980 A1 | 3/2007 | Strother et al. | |
| 2007/0129767 A1* | 6/2007 | Wahlstrand | 607/33 |
| 2007/0279002 A1 | 12/2007 | Partovi | |
| 2008/0172109 A1 | 7/2008 | Rahman et al. | |
| 2008/0312530 A1* | 12/2008 | Malackowski et al. | 600/426 |
| 2009/0069869 A1 | 3/2009 | Stouffer et al. | |
| 2009/0112291 A1 | 4/2009 | Wahlstrand et al. | |
| 2009/0118796 A1 | 5/2009 | Chen et al. | |

OTHER PUBLICATIONS

International Search Report and Written Opinion regarding corresponding patent application No. PCT/US2010/040935, dated Sep. 10, 2010.
U.S. Appl. No. 12/368,385, filed Feb. 10, 2009, Aghassian.

* cited by examiner

*Primary Examiner* — Nicole F Lavert
(74) *Attorney, Agent, or Firm* — Wong, Cabello, Lutsch, Rutherford & Brucculeri, LLP

(57) ABSTRACT

By incorporating magnetic field sensing coils in an external charger, it is possible to determine the position of an implantable device by sensing the reflected magnetic field from the implant. In one embodiment, two or more field sensing coils are arranged to sense the reflected magnetic field. By comparing the relative reflected magnetic field strengths of the sensing coils, the position of the implant relative to the external charger can be determined. Audio and/or visual feedback can then be communicated to the patient to allow the patient to improve the alignment of the charger.

19 Claims, 19 Drawing Sheets

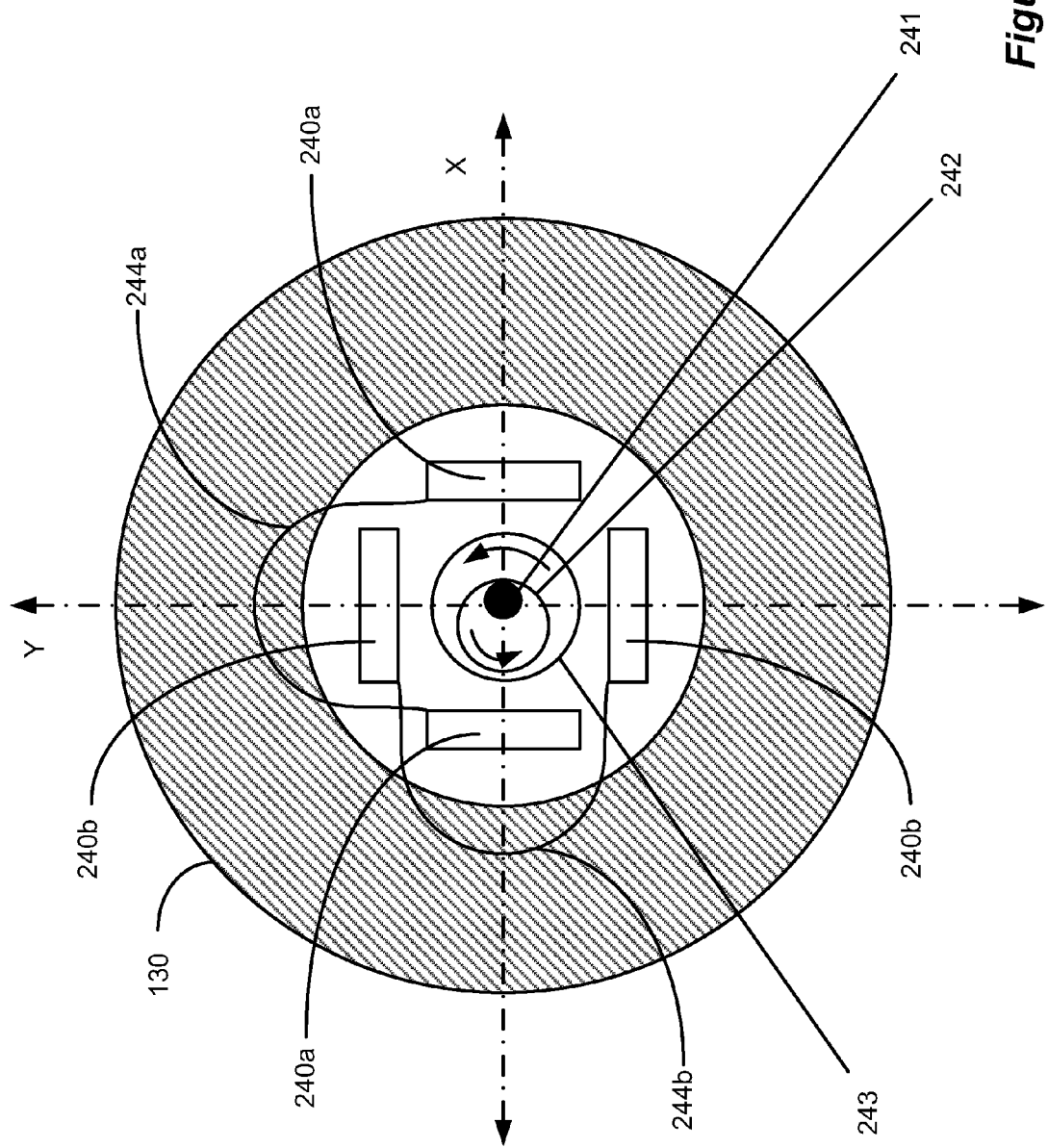

EXTERNAL CHARGER FOR A MEDICAL IMPLANTABLE DEVICE USING FIELD SENSING COILS TO IMPROVE COUPLING

FIELD OF THE INVENTION

The present invention relates to techniques for providing improved alignment between an external charger and an implantable device.

BACKGROUND

Implantable stimulation devices generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The present invention may find applicability in all such applications, although the description that follows will generally focus on the use of the invention within a Spinal Cord Stimulation (SCS) system, such as that disclosed in U.S. Patent Application Publication 2007/0038250.

Spinal cord stimulation is a well-accepted clinical method for reducing pain in certain populations of patients. An SCS system typically includes an Implantable Pulse Generator (IPG), electrodes, at least one electrode lead, and, optionally, at least one electrode lead extension. As shown in FIG. 1, the electrodes 106, which reside on a distal end of the electrode lead 102, are typically implanted along the dura 70 of the spinal cord 19, and the IPG 100 generates electrical pulses that are delivered through the electrodes 106 to the nerve fibers within the spinal column 19. Electrodes 106 are arranged in a desired pattern and spacing to create an electrode array 110. Individual wires 112 within one or more electrode leads 102 connect with each electrode 106 in the array 110. The electrode lead(s) 102 exit the spinal column 19 and may attach to one or more electrode lead extensions 120. The electrode lead extensions 120, in turn, are typically tunneled around the torso of the patient to a subcutaneous pocket where the IPG 100 is implanted. Alternatively, the electrode lead 102 may directly connect with the IPG 100.

As should be obvious, an IPG needs electrical power to function. Such power can be provided in several different ways, such as through the use of a rechargeable or non-rechargeable battery or through electromagnetic (EM) induction provided from an external charger, or from combinations of these and other approaches, which are discussed in further detail in U.S. Pat. No. 6,553,263 ("the '263 patent"). Perhaps the favorite of these approaches is to use a rechargeable battery in the IPG, such as a lithium-ion battery or a lithium-ion polymer battery. Such a rechargeable battery can generally supply sufficient power to run an IPG for a sufficient period (e.g., a day or more) between recharging. Recharging can occur through the use of EM induction, in which EM fields are sent by an external charger to the IPG. Thus, when the battery needs recharging, the patient in which the IPG is implanted can activate the external charger to transcutaneously (i.e., through the patient's flesh) charge the battery (e.g., at night when the patient is sleeping or during other convenient periods).

The basics of such a system are shown in FIG. 2. As shown, the system comprises, in relevant part, the external charger 208 and IPG 100. A primary coil 130 in the charger 208 produces an EM field 290 capable of transcutaneous transmission through a patient's flesh 278. The external charger 208 may be powered by any known means, such as via a battery or by plugging into a wall outlet, for example. The EM field 290 is met at the IPG 100 by another coil 270, and accordingly, an AC voltage is induced in that coil 270. This AC voltage in turn is rectified to a DC voltage at a rectifier 682, which may comprise a standard bridge circuit. (There may additionally be data telemetry associated with the EM field 290, but this detail is ignored as impertinent to the present disclosure). The rectified DC voltage is, in turn, sent to a charge controller and protection circuit 684, which operates generally to regulate the DC voltage and to produce either a constant voltage or constant current output as necessary for recharging the battery 180.

FIG. 3 shows further details of external charger 208 with the top portion of the housing removed. Further details concerning external chargers can be found in U.S. Patent Application Publication 2008/0027500. As shown in FIG. 3, electrical current 114 flowing in a counterclockwise direction through the primary coil 130 induces a magnetic field 290 having a prominent portion in a direction perpendicular to the plane in which the primary coil 130 lies. Primary coil 130 is typically formed of many turns of copper Litz wire, but the individual turns are not shown in FIG. 3 for clarity. Thus, when a face of the case of the external charger 208 is oriented in close proximity to an implanted device, such that the primary coil 130 is parallel to a corresponding coil within the IPG 100, the magnetic field generated by the primary coil 130 induces an electrical current within a corresponding coil to charge a battery within, or otherwise provide power, to the IPG 100.

This system is akin to a transformer where the primary coil is in the external charger 208 and secondary coil in the IPG 100. The efficiency of this coupling is largely dependent upon the alignment between the two coils, which efficiency can be expressed as a coupling factor, k. Achieving a good coupling factor is essential for optimizing efficiency of the inductive link. Not only does good coupling increase the power transferred to the implant, it minimizes heating in the implant, and also reduces the power requirements of the external charger, which reduces heating of the charger and allows a smaller form factor. Proper coupling is also essential if there is to be any data telemetry between the external charger 208 and the implant.

Operation of the external charger 208 in the prior art typically involves the use of audio feedback to the user. Thus, when charging begins, the external charger 208 produces induced field 290 and begins searching for the IPG 100, as will be explained in more detail herein. An audio transducer in the external charger 208 would provide an intermittent audible sound (e.g., beeping) when coupling was poor between the charger 208 and the IPG 100, which beeping would alert the user to move the external charger relative to the IPG. Once the positioning and coupling were improved, the charger 208 would stop beeping, and the location of the charger 208 would be held in place over the IPG 100 by using double-side adhesive pads or a belt. If the charger 208 again became poorly positioned relative to the IPG 100, the audio transducer would again start beeping, so that the position of the charger 208 relative to the IPG 100 could again be readjusted. A back-telemetry link from the IPG 100 would communicate to the charger 208 when the IPG battery was fully charged, which condition can again be audibly signaled to the patient.

As noted earlier, proper alignment between an external charger and an implant is essential for proper system function, energy transfer, and safety to the patient. However, this has heretofore been difficult to achieve. In particular, it has been noticed by the inventors that it is difficult for prior art external chargers to differentiate between a deeply-implanted device that is well aligned with respect to the charger, and a shallowly-implanted device that is poorly aligned with respect to the charger. Either scenario appears the same to the external charger 208. As a result, the patient will only know that the coupling is poor, but will not know how to remedy this situation apart from trial-and-error re-positioning of the charger.

Given these shortcomings, the art of implantable devices would benefit from techniques for achieving improved coupling between an external charger and an implantable device that provide: the ability to accurately indicate the relative position of the charger to the implant; increased charging efficiency; faster charging rates; increased patient safety and comfort; lower power requirements; and a smaller form factor. This disclosure presents such a solution.

BRIEF DESCRIPTION OF THE DRAWINGS

FIG. 6C shows a top down view of a system comprising an improved external charger for an implantable medical device.

DETAILED DESCRIPTION

The description that follows relates to use of the invention within a spinal cord stimulation (SCS) system. However, it is to be understood that the invention is not so limited. Rather, the invention may be used with any type of implantable medical device that could benefit from improved alignment between an external charger and the implantable device. For example, the present invention may be used as part of a system employing an external charger configured to charge a pacemaker, an implantable pump, a defibrillator, a cochlear stimulator, a retinal stimulator, a stimulator configured to produce coordinated limb movement, a cortical or deep brain stimulator, or in any other stimulator configured to treat urinary incontinence, sleep apnea, shoulder sublaxation, etc. Moreover, the technique can be used in non-medical and/or non-implantable devices or systems as well, i.e., in any device or system in which proper coupling between a primary and second device is necessary or desirable.

As noted earlier, achieving proper coupling between an external charger and an implant can be difficult, as it is hard for the external charger to differentiate between a deep implant that is well aligned to the external charger and a shallow implant that is misaligned with the external charger. Both scenarios appear the same to the external charger. The present invention provides an improved external charger having improved means for determining the position of the implanted device relative to the charger by sensing the magnetic field reflected from the implanted device.

In one embodiment, the external charger 208 contains magnetic field sensing coils to help discriminate between deep implants and misaligned implants. Through use of these magnetic field sensing coils, it is possible to determine the position of an implantable device by sensing the reflected magnetic field from the implant. In one embodiment, three or more field sensing coils are arranged within the charge coil in a plane or planes parallel to the charge coil. In another embodiment, two or more field sensing coils are arranged within the charge coil in one or more planes perpendicular to the charge coil. By comparing the relative reflected magnetic field strengths of the sensing coils, the position of the implant can be determined. Audio and/or visual feedback can then be communicated to the patient to allow the patient to improve the alignment of the charger.

Figure 4A:
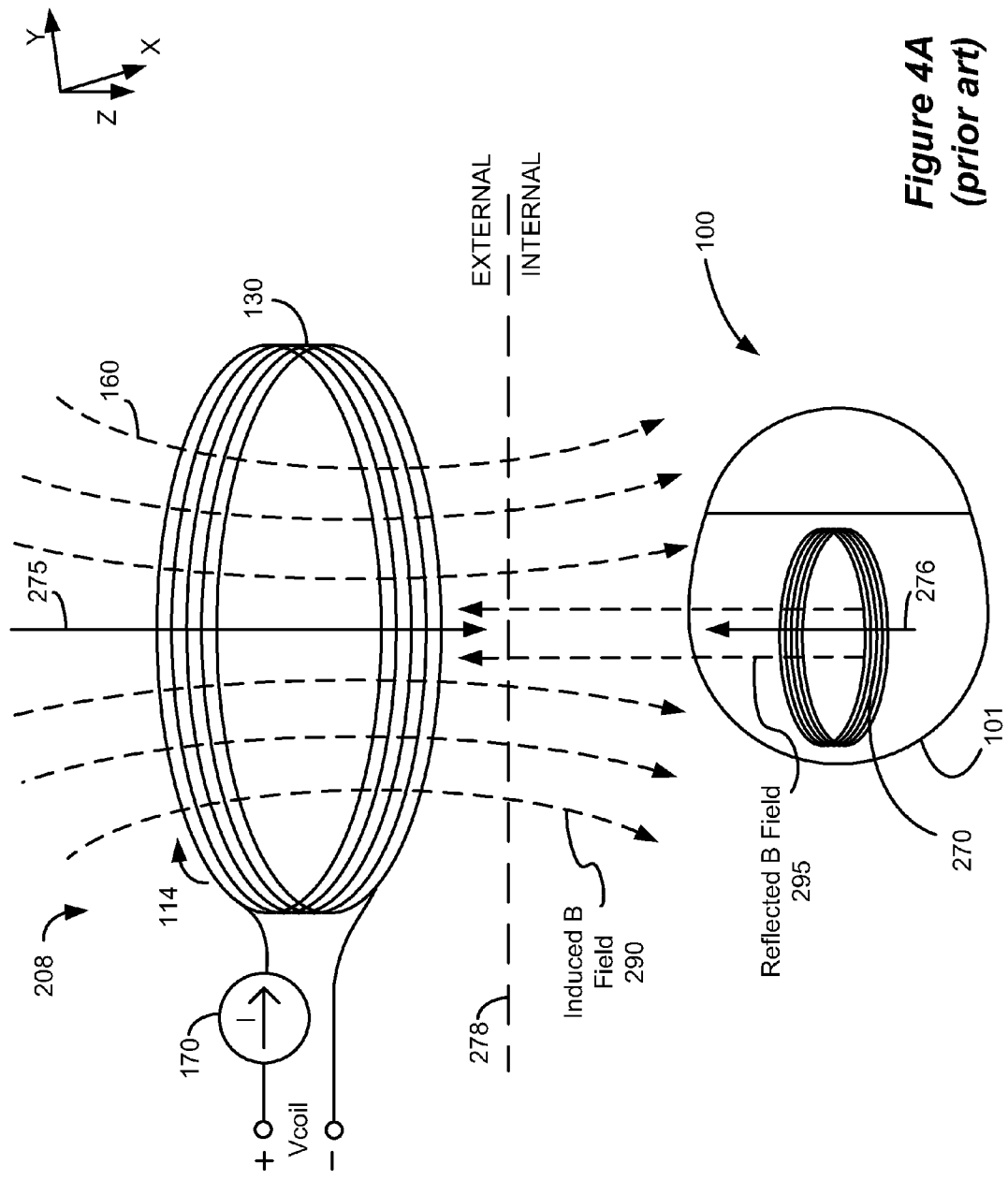
FIGS. 4A-4C illustrate typical configurations, wherein the primary coil of a prior art external charging device is located at or near the outer surface of the patient's skin and the secondary coil of an implantable medical device is located near to or far from the inner surface of the patient's skin.

FIG. 4A shows a primary coil 130 configured for transcutaneously charging the IPG 100 via inductive coupling in accordance with the prior art. As mentioned earlier, the charger 208 comprises a primary coil 130, through which an AC current 114 is passed via an AC current source 170. This current 114 produces induced magnetic field 290, which is illustrated as a plurality of flux lines 160. Flux lines 160 are essentially perpendicular to the surface of the skin 278 where they pass through its surface. In addition, the magnetic flux lines 160 near the center of the primary coil 130 are substantially parallel to the central axis 275 of the coil. A corresponding coil 270 within the IPG 100 transforms this magnetic energy into an electrical current, which is rectified and used by circuitry to charge a battery 180 within the IPG 100 as explained previously. The distance between the charger 208 and the IPG 100 is typically on the order of about 1-5 centimeters.

The primary and secondary coils 130 and 270 are substantially in the shape of a circular loop, and are typically formed of several turns of wire, as one skilled in the art will appreciate. However, it will be recognized that the substantially circular shape of the coils 130 and 270 are merely illustrative. The turns of the primary coil 130 define a center opening or aperture having a central axis 275. It will be recognized that the surface of the skin 278 is not always flat. Hence, the central axis 275 of the primary coil 130 is sometimes only approximately or substantially perpendicular to the surface of the skin 278.

The induced magnetic field 290 produces eddy currents in the IPG's typically metallic case 101 or in other conductive structures within the IPG 100. Such eddy currents operate to produce a reflected magnetic field 295, which operates to change the mutual inductance of the primary coil 130, effectively "detuning" the coil. Such detuning changes Vcoil, the voltage used to produce the current in the primary coil 130. Accordingly, from monitoring Vcoil, the relative coupling between the external charger 208 and the IPG 100 can be inferred. Vcoil decreases as the coupling increases, which generally occurs when the external charger 208 and the IPG 100 are closer to one another.

Figure 4C:
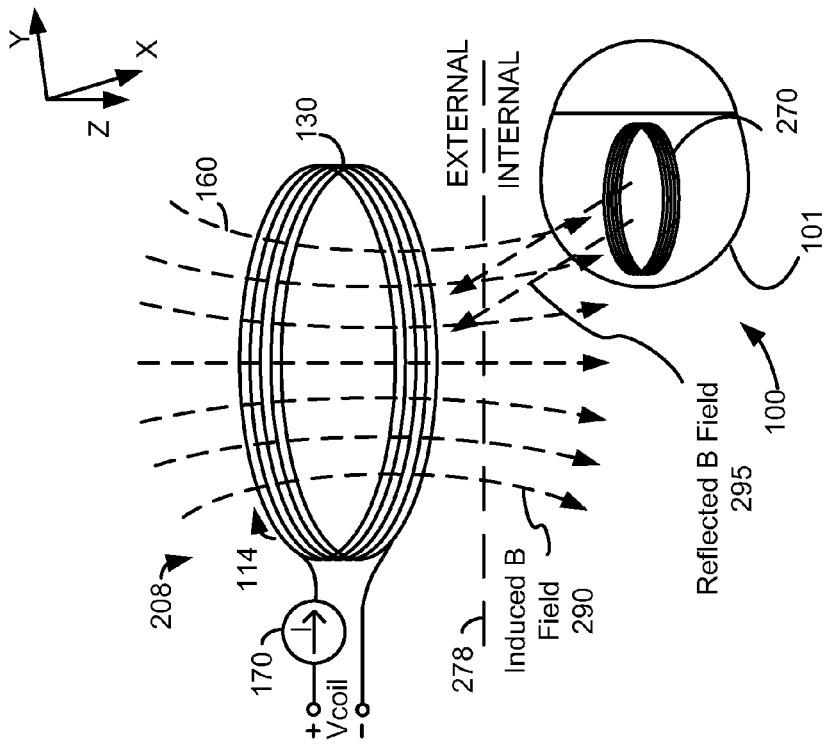
Figure 4B:
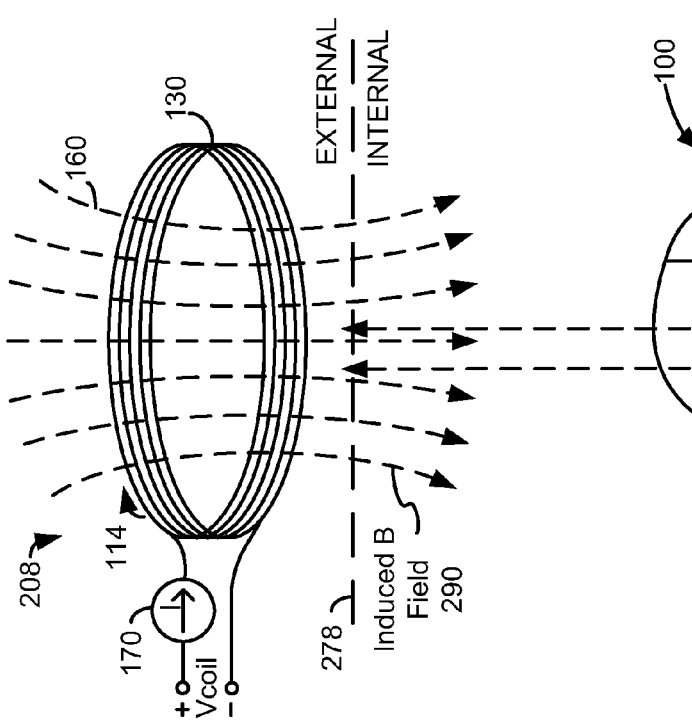

However, this means of monitoring coupling between the external charger 208 and the IPG 100 cannot discern between distance and misalignment, which conditions are illustrated in FIGS. 4B and 4C. FIG. 4B shows an IPG 100 implanted relatively deeply within a patient, but otherwise well aligned from an axial perspective, i.e., coil axes 275 and 276 (see FIG. 4A) are not offset from each other. FIG. 4C, by contrast, shows an IPG 100 implanted relatively shallowly with a patient, but with poor alignment, i.e., coil axes 275 and 276 (see FIG. 4A) are offset to a large degree. In either of these cases, the coupling between the external charger and the IPG 100 will be relatively poor, with the result that Vcoil will not be greatly affected by the IPG 100. However, because Vcoil might be the same in magnitude for both conditions, Vcoil cannot be used to discern between depth (FIG. 4B) and misalignment (FIG. 4C). As a result, Vcoil cannot be used by the external charger 208—and ultimately the patient—to qualify the reason for poor coupling, or how to fix the poor coupling by appropriate repositioning of the external charger 208.

Figure 5A:
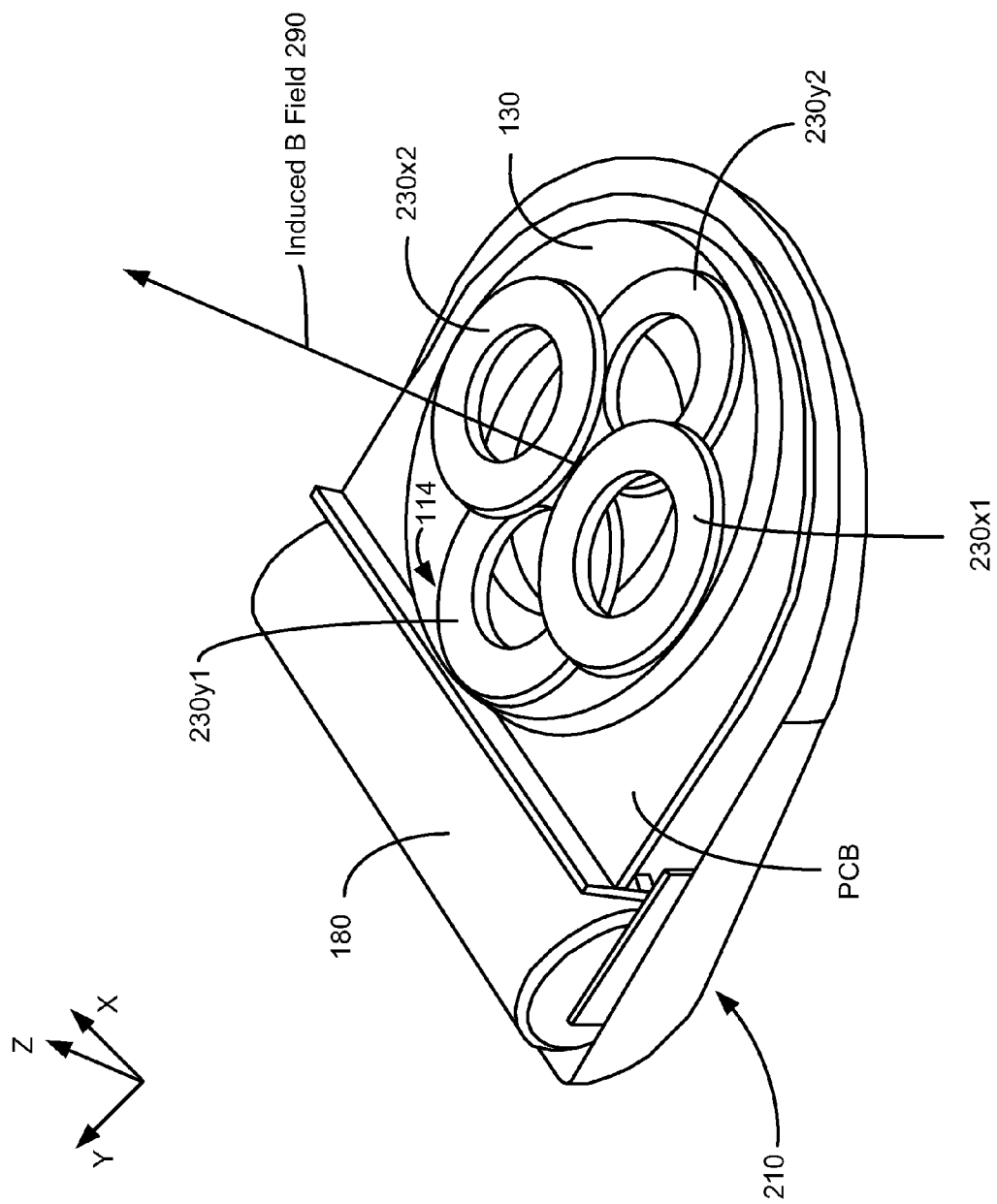
FIG. 5A shows a perspective view of one possible embodiment of an improved external charger for an implantable medical device.

FIG. 5A shows one embodiment of an improved external charger 210 with the ability to determine the relative position of an implanted device, and thus maximize coupling by indicating to the user how to improve charger/device alignment. In this embodiment, four field sensing coils 230 are arranged into two pairs, 230x and 230y, of two connected sensing coils each. Each of the pairs of sensing coils 230x and 230y are positioned within primary coil 130 and such that the plurality of sensing coils are wound around axes that are parallel to the central axis 275 (FIG. 5B).

The field sensing coils 230 are designed to detect the amount of the reflected magnetic field 295 passing through them. Each pair 230x and 230y straddles the central axis 275 (FIG. 5B) of the primary coil 130, such that the coils in each pair are equidistant from the central axis 275 and opposite each other. As shown, the pairs 230x and 230y are positioned orthogonally with respect to each other. FIG. 5B shows a primary coil 130 configured for transcutaneously charging the IPG 100 via inductive coupling with sensing coils 230 arranged in accordance with the embodiment shown in FIG. 5A. As is explained in greater detail below, by comparing electrical measurements, such as the reflected magnetic field strengths induced in each sensing coil 230 of each pair of sensing coils, 230x and 230y, the position of the implant in both the x- and y-directions can be determined by the external charger 210's position indication circuitry 279 (FIGS. 5C-5F). Audio and/or visual feedback of the implant position can then be communicated to the patient to improve alignment of the charger.

Figure 5B:
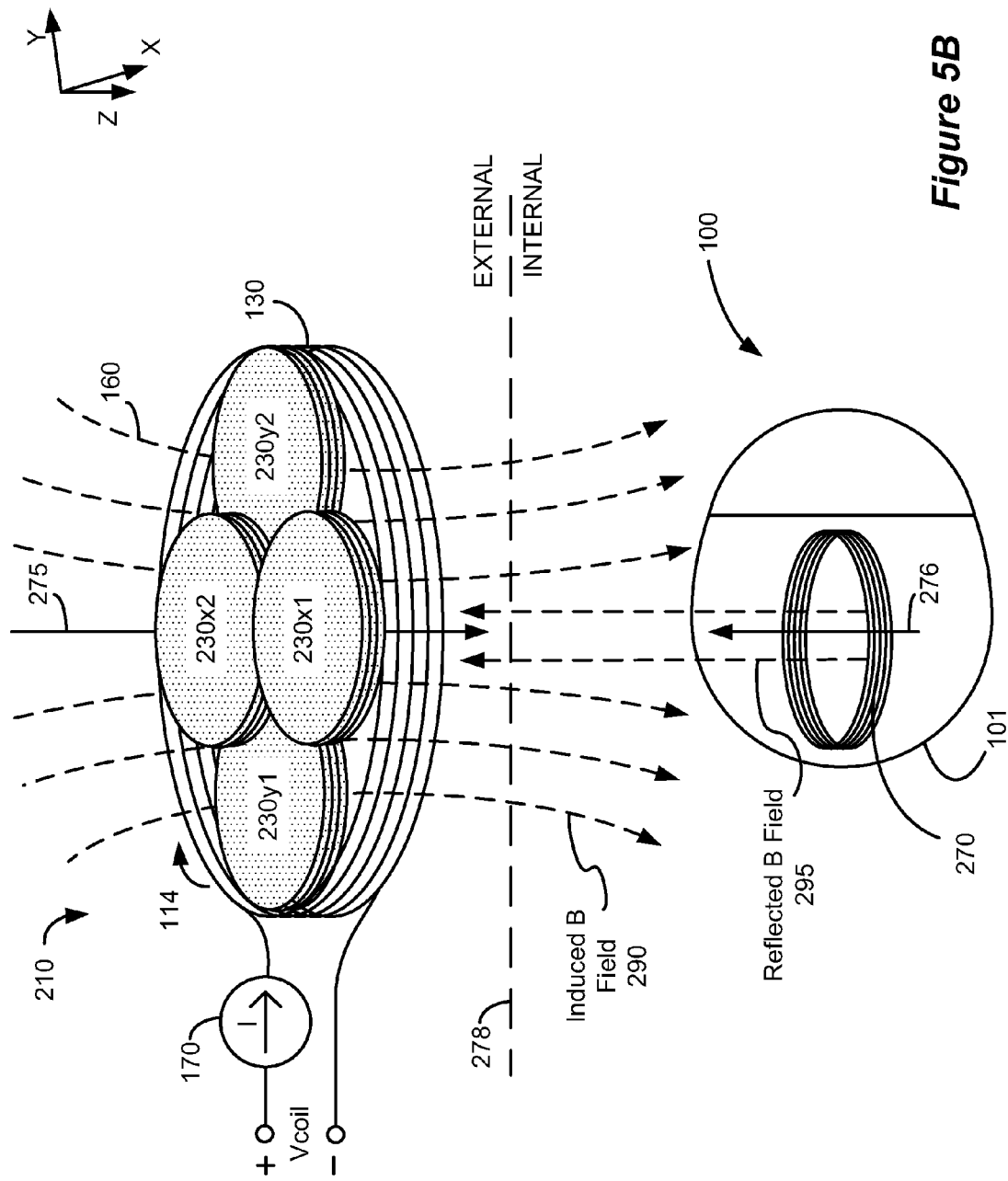
FIG. 5B shows a typical configuration, wherein the primary coil of an improved external charging device is located at or near the outer surface of the patient's skin and the secondary coil of an implantable medical device is located near the inner surface of the patient's skin.
Figure 5C:
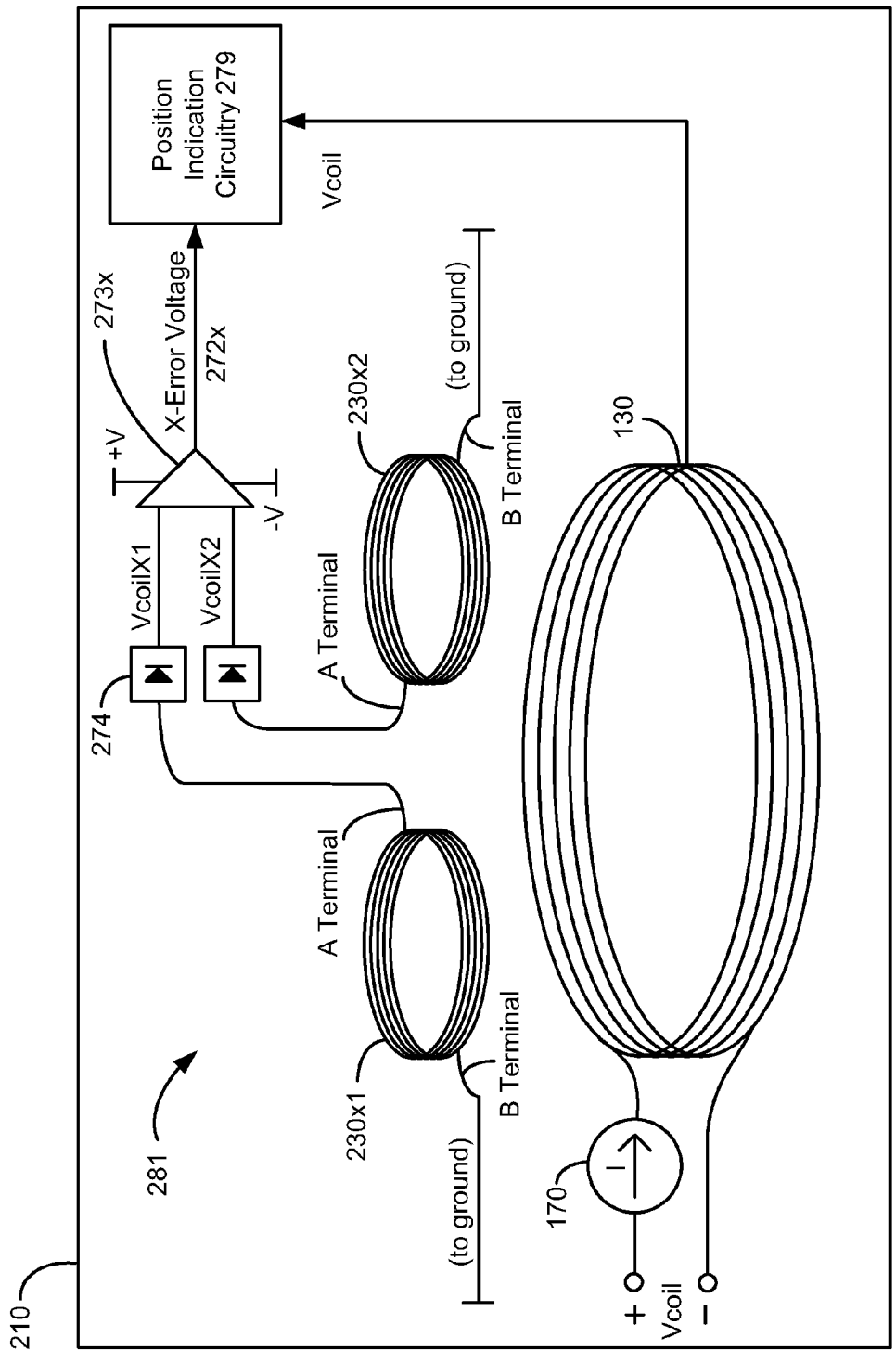
FIG. 5C shows two sensing coils whose outputs are sent to an instrumentation amplifier.

In the embodiment of FIG. 5C, alignment of the primary coil 130 relative to the IPG 100 is determined by alignment sensing circuitry 281. The output of alignment sensing circuitry 281, comprising x- and y-error voltages 272x and 272y, is provided to a position indication circuitry 279, which indicates to the user the misalignment of the external charger 210 relative to the implantable medical device. Such means of indicating misalignment to the user will be discussed further below.

Figure 5D:
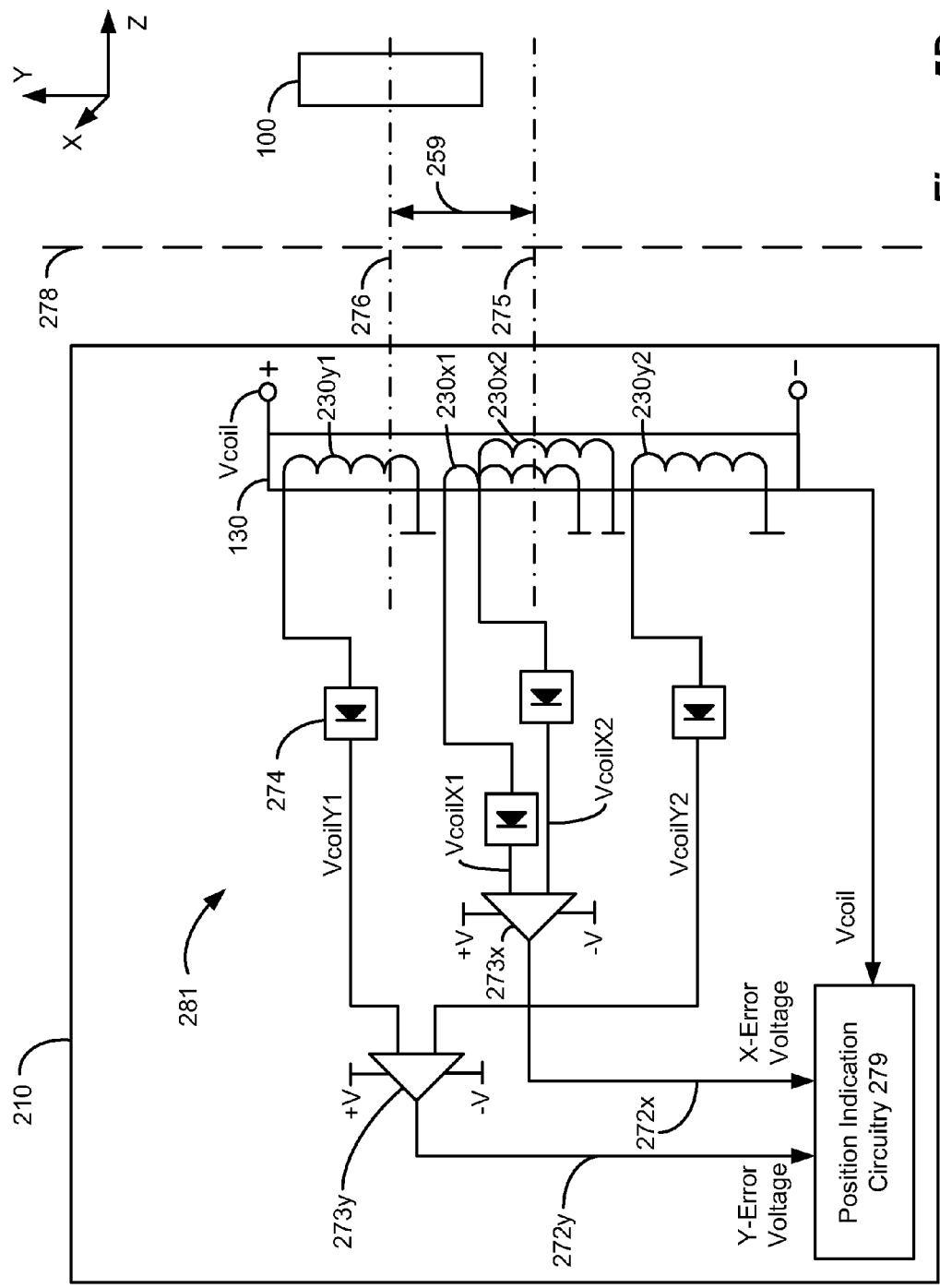
FIG. 5D shows a block diagram of circuitry for a system comprising an improved external charger for an implantable medical device.

FIG. 5C shows one potential arrangement of a pair of sensing coils 230x for the improved external charger 210 that is depicted in FIGS. 5A and 5B. In this embodiment, only sensing coils 230x1 and 230x2—which are used to determine the IPG 100's misalignment with the external charger 210 in the x-direction—are shown for the sake of simplicity. A complete external charger 210 utilizing this embodiment will also have a corresponding pair of sensing coils 230y1 and 230y2 to measure misalignment in the y-direction, as is seen in FIG. 5D and explained in further detail below. In the embodiment of FIG. 5C, the sensing coils 230x and 230y are not connected to each other, i.e., each sensing coil 230x has one terminal connected to ground and the other terminal connected to a detector 274 that outputs a signal indicative of the voltage measured at each sensing coil 230x. Each detector 274 may be implemented as a half-wave rectifier using a single diode, for example.

The output signal from each detector 274 in a sensing coil pair, e.g., VcoilX1 and VcoilX2, is then sent to an instrumentation amplifier 273x which, as is known to one of skill in the art, amplifies the difference between the two signals fed into it. The output 272x of the instrumentation amplifier 273x is an error indication signal, also known as an "error voltage." The error voltages indicate alignment of the external charger 210 and the implantable medical device 100 with respect to a particular direction. In the case of x-error voltages and y-error voltages, the directions are perpendicular to each other. In the embodiment of FIGS. 5C and 5D, the voltages across each sensing coil within each sensing coil pair are compared to each other to produce an error voltage with respect to a particular direction. In other words, alignment sensing circuitry 281 derives a first indicator and a second indicator, wherein the first and second indicators indicate misalignment with respect to first and second directions. The outputs 272x and 272y are then converted from analog signals into digital signals and then sent to the improved external charger 210's position indication circuitry 279 so that the location of the implantable medical device 100 can be determined and appropriate instruction can be delivered to the user as to how to improve the external charger 210's alignment with the implantable medical device 100.

FIG. 5D shows a circuit diagram depicting the alignment sensing circuitry 281 of the improved external charger 210 depicted in FIG. 5C. As mentioned above in reference to FIG. 5C, each sensing coil 230 in the external charger 210 is connected to a detector 274. The output signal from each detector 274 in a "sensing coil pair," e.g., the detectors measuring the voltage at sensing coils 230x1 and 230x2 (which output signals are labeled in FIG. 5D as VoilX1 and VcoilX2, respectively), is then sent to an instrumentation amplifier 273x which, as explained above, amplifies the difference between the two signals fed into it.

If IPG 100 is closer in the x-direction to sensing coil 230x1 than it is to sensing coil 230x2, the voltage detected at sensing coil 230x1 will be lower, say 50V, than the voltage detected at sensing coil 230x2, say 52V. This difference of positive two volts (VcoilX2−VcoilX1) will cause instrumentation amplifier 273x to output a positive voltage signal. If instead, the IPG 100 is closer in the x-direction to sensing coil 230x2, the voltage at sensing coil 230x1 will be higher, say 52V, than the voltage detected at sensing coil 230x2, say 50V. In this case, the difference of negative two volts will cause instrumentation amplifier 273x to output a negative voltage signal. In other words, the magnitude of the signal output by instrumentation amplifier 273x is directly proportional to the difference in magnitude between VcoilX1 and VcoilX2. The magnitude of the difference also indicates relative closeness of the primary coil 130 and the IPG 100. For example, if the voltages measured at 230x1 and 230x2 were 45V and 57V, respectively, instead of 50V and 52V as in the example above, the difference between the signals would be 12V, and the magnitude of the signal output by instrumentation amplifier 273x would be greater than in the 52V/50V example. The greater output by instrumentation amplifier 273x in the 45V/57V example would indicate to position indication circuitry 279 that IPG 100 was located even further towards sensing coil 230x1 in the 45V/57V scenario than it was in the 50V/52V scenario. Thus, this embodiment is able to provide detailed information about the IPG 100's relative location in the x-direction. As will be understood, the same processing is simultaneously being carried out by sensing coils 230y1 and 230y2 to determine the IPG 100's relative location in the y-direction, thus allowing external charger 210 to give a complete picture of IPG 100's location.

However, because the sensing coils 230 in this embodiment are arranged in the same plane as the primary coil 130, the measured magnetic field strength will have a large bias due to coupling from the primary coil 130. In the example given above with respect to FIG. 5D, the difference between 52V and 50V is not very large (i.e., 2V) when compared to the absolute voltages being measured on the sensing coils. Thus, it can be difficult to rapidly calculate the difference between the voltages of the two sensing coils with a high degree of resolution.

Figure 5E:
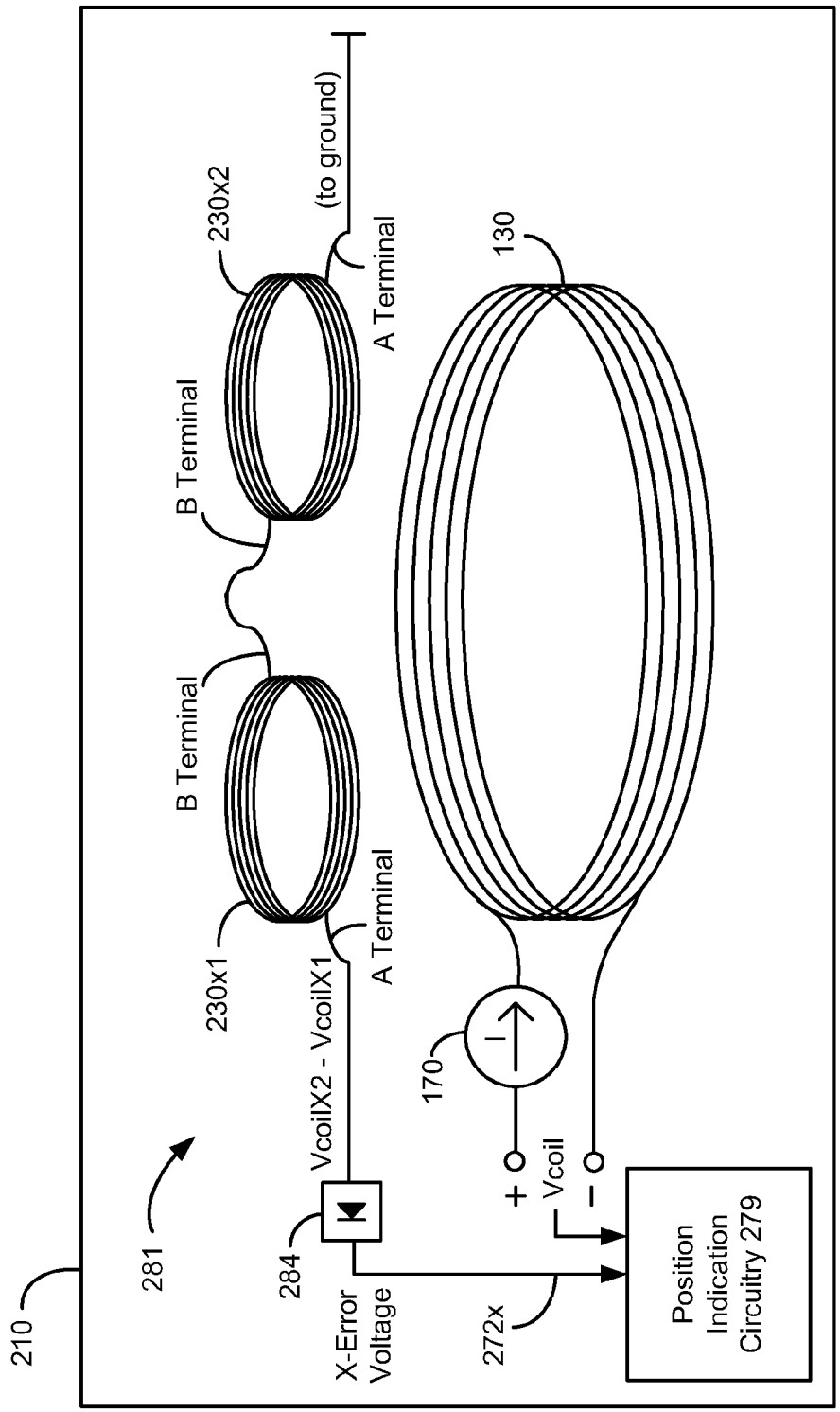
FIG. 5E shows two sensing coils connected in series and end-to-end.
Figure 5F:
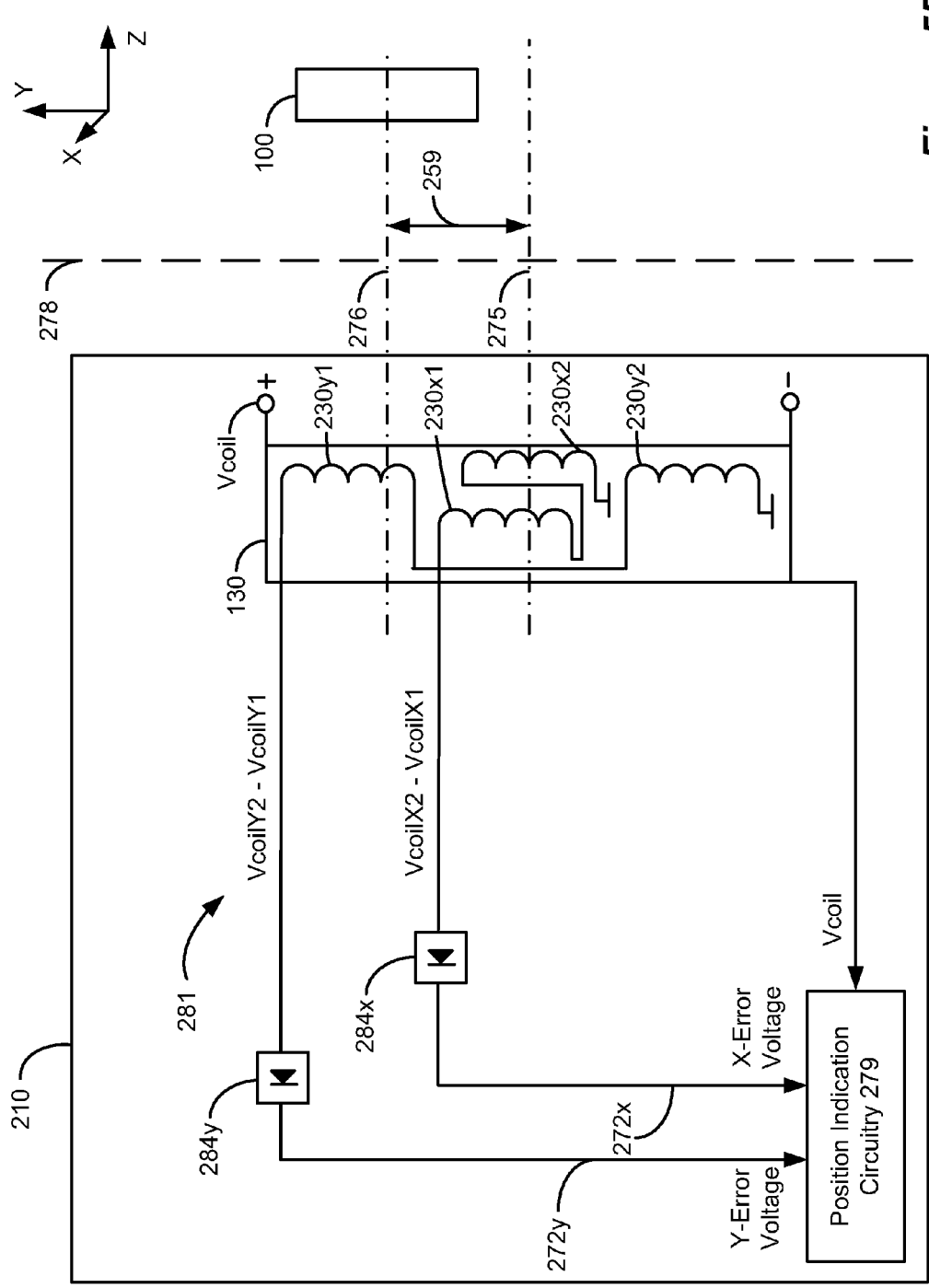
FIG. 5F shows a block diagram of circuitry for a system comprising an improved external charger for an implantable medical device.

Another embodiment, as shown in FIGS. 5E and 5F, presents a solution to this issue. Specifically, the sensing coils 230x1 and 230x2 in this embodiment are connected to each other in series and "end-to-end." The term 'end-to-end,' as used herein, simply means that the end of one sensing coil, i.e., the 'B' Terminal as shown in FIG. 5E, is connected to the end, i.e., 'B' Terminal, of another sensing coil. Alternatively, the beginning of one sensing coil, i.e., the 'A' Terminal as shown in FIG. 5E, could be connected to the beginning, i.e., 'A' Terminal, of another sensing coil. The terms "beginning" and "end"—and the designations 'A' Terminal and 'B' Terminal—are relative to the sensing coil, and are defined by the direction of the induced magnetic field, which should be the same for each sensing coil in a sensing coil pair. Connecting the sensing coils end-to-end in that manner cancels out the common mode AC voltage between sensing coil 230x1 and sensing coil 230x2. In other words, the voltage measured on the 'A' terminal of sensing coil 230x1 will be the difference of the voltages across sensing coils 230x1 and 230x2. The manner in which the coils are connected essentially performs the work of the instrumentation amplifier 273, which was described above in reference to FIGS. 5C and 5D, thus obviating the need for instrumentation amplifiers in this embodiment.

With respect to the 52V/50V example given above in relation to the embodiment of FIGS. 5C and 5D, the embodiment of FIGS. 5E and 5F would simply output a 2V signal to synchronous detector 284. This would very clearly be a non-zero signal, indicating misalignment of the external charger 210 and the IPG 100. There would be no need to compare two different, relatively large voltage measurements and amplify the resulting difference with enough resolution to get meaningful information, as was done in the embodiment of FIGS. 5C and 5D. The only measurement that needs to be taken in the embodiment of FIGS. 5E and 5F is the magnitude of the output voltage for each sensing coil pair. As would be expected, this embodiment would result in a net voltage of zero at synchronous detector 284 when IPG 100 is centered symmetrically with respect to sensing coils 230x1 and 230x2. As would be understood by one of skill in the art, synchronous detector 284 will also need to be connected to a timing reference signal, which is not shown for simplicity.

The outputs 272x and 272y of each synchronous detector 284x and 284y, are error indication signals, also known as an "error voltages." The error voltages indicate alignment of the external charger 210 and the implantable medical device 100 with respect to a particular direction. In the case of x-error voltages and y-error voltages, the directions are perpendicular to each other. In this embodiment, the voltages across each sensing coil pair are measured to produce an error voltage with respect to a particular direction. The error voltages are then converted from an analog signal into a digital signal and sent to the improved external charger 210's position indication circuitry 279 so that the location of the implant 100 can be determined and appropriate instructions can be delivered to the user as to how to improve the charger 210's alignment with IPG 100.

Figures 5G, 5H:
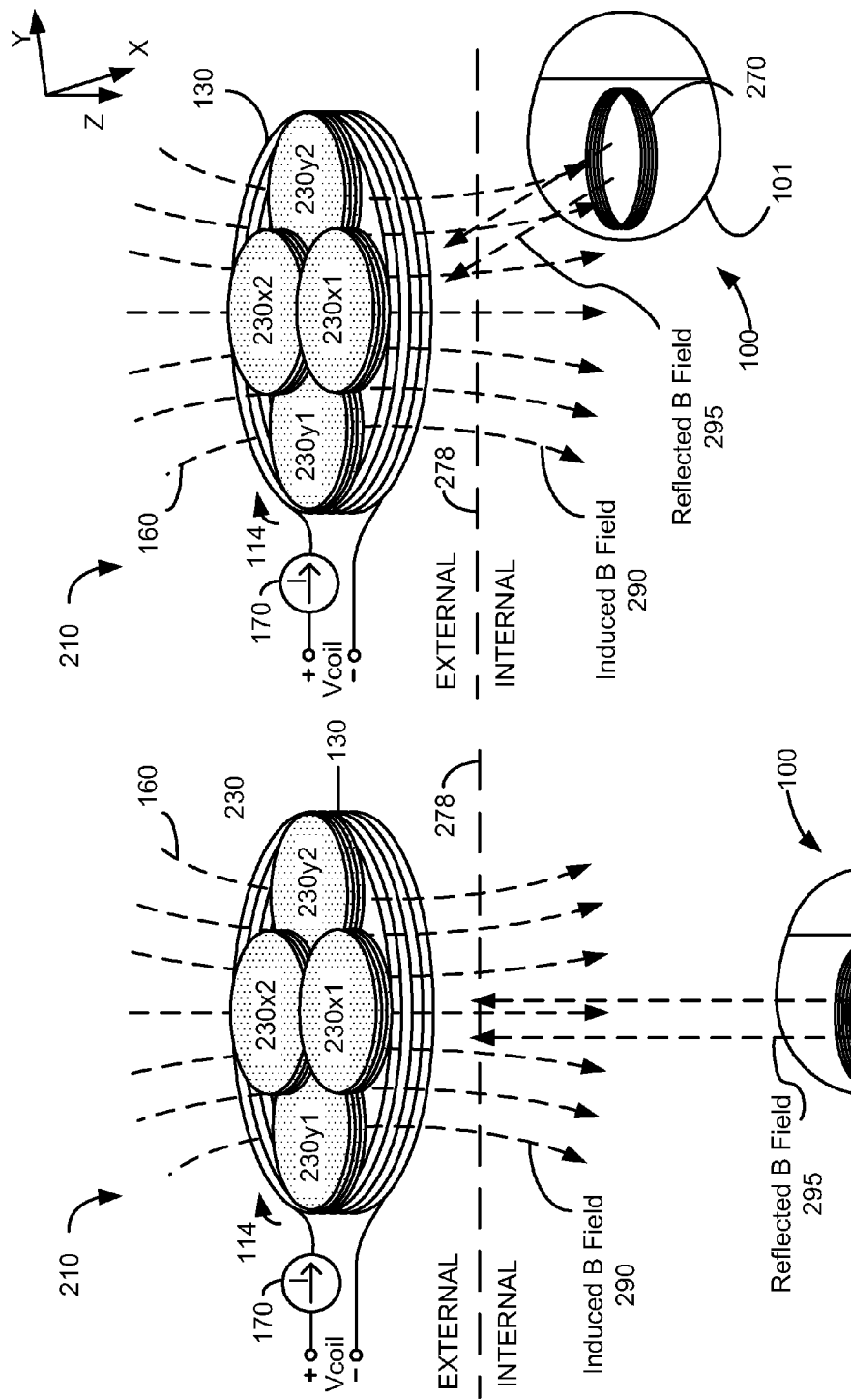
FIGS. 5G-5H illustrate typical configurations, wherein the primary coil of an improved external charging device is located at or near the outer surface of the patient's skin and the secondary coil of an implantable medical device is located near to or far from the inner surface of the patient's skin.

FIG. 5G shows a scenario where an implantable medical device 100 is deeply implanted in the patient's body but well aligned with external charger 210. In this scenario, each of the field sensing coils 230 would have a similar Vcoil because each coil would pick up an equivalent reflected magnetic flux, i.e., VcoilX1, VcoilX2, VcoilY1, and VcoilY2 would all be equal. Thus, the differences between the measured voltages of the two sensing coils in each of the sensing coil pairs would be close to zero, and the position indication circuitry 279 would determine that the external charger 210 was properly, i.e., symmetrically, aligned with the IPG 100.

FIG. 5H shows a scenario where an implantable medical device 100 is shallowly implanted in the patient's body but poorly aligned with external charger 210; specifically, it is skewed in the y-direction. As discussed above, a prior art external charger would not be able to distinguish between the scenario presented in FIG. 5G and the scenario presented in FIG. 5H. However, with the improved external charger 210, these two scenarios are distinguishable. In the scenario shown in FIG. 5H, field sensing coil 230y2 measures a lower Vcoil (VcoilY2) than sensing coil 230y1 (VcoilY1) because sensing coil 230y2 picks up a disproportionately larger amount of reflected magnetic flux. As was discussed above, the alignment sensing circuitry 281 compares the VcoilY1 and VcoilY2 values. In this scenario, it would result in a determination that VcoilY2 is smaller than VcoilY1 and alignment sensing circuitry 281 would output a negative "Y-error voltage" value 272y. This signal would then be converted into a digital signal, sent to position indication circuitry 279, and interpreted to mean that the IPG 100 was actually closer to sensing coil 230y2 than it was to sensing coil 230y1, i.e., that the charger 210 was too far to the left as illustrated. The external charger 210 would then indicate to the user how to correct the alignment problem, i.e., by instructing the user to move the charger 210 to the right, to maximize the electrical coupling of external charger 210 and implantable medical device 100. The same processing is simultaneously carried out by sensing coils 230x1 and 230x2 to report information about the IPG 100's location in the x-direction.

Sometimes, the reflected magnetic field 295 from the implanted device 100 is not very strong, especially when the implanted device 100 is implanted deeply within the patient. Thus, it can be difficult to detect very small differences in the voltages across each of the sensing coils 230. The resolution of the measurements may have to be high for the circuitry to be able to notice the small differences in voltage. Additionally, due to the constantly changing nature of the electric field caused by the user's breathing and heart beat, the signal from all sensing coils 230 should be measured nearly simultaneously for a proper comparison.

Figure 6A:
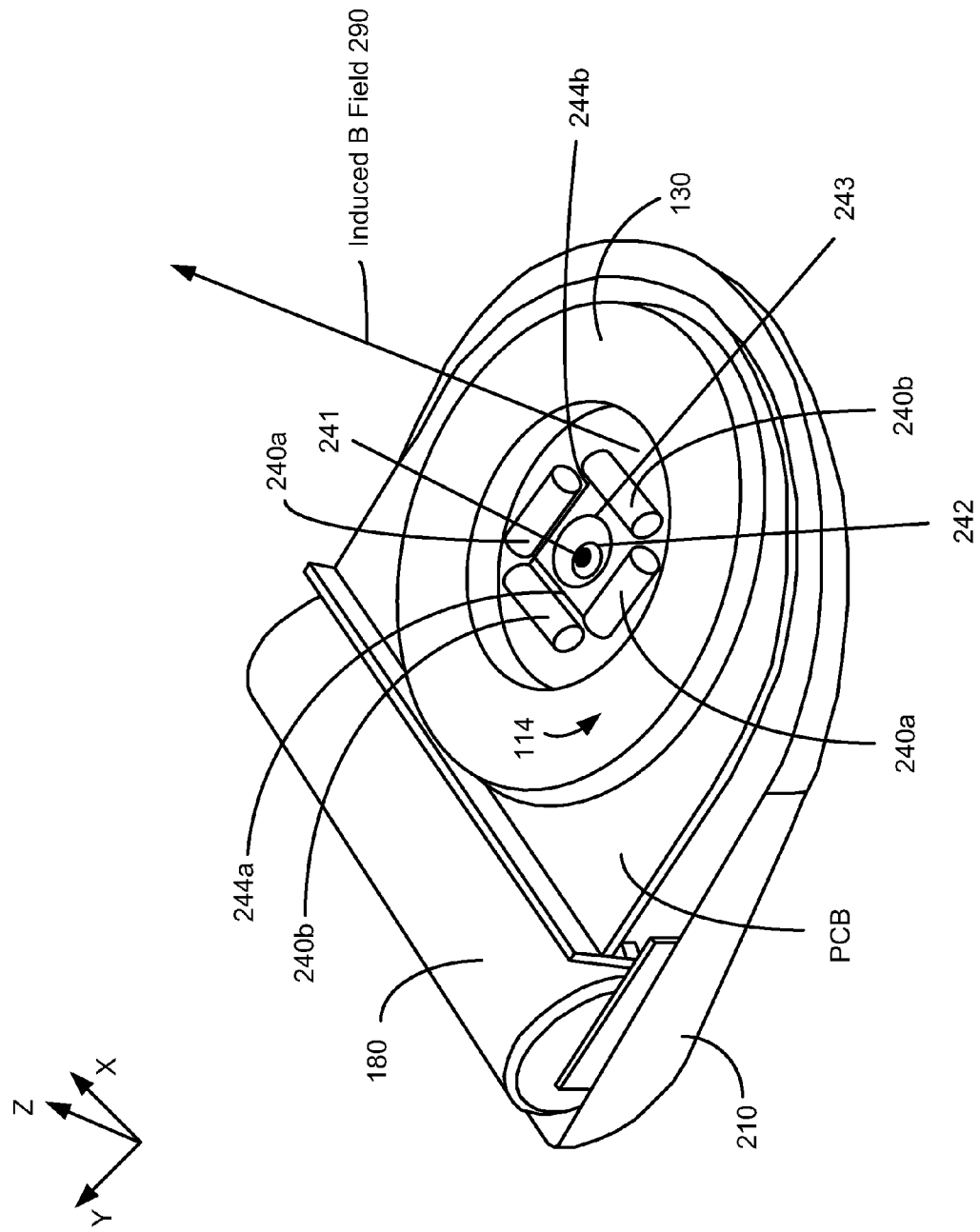
FIG. 6A shows a perspective view of another embodiment of an improved external charger for an implantable medical device.

FIG. 6A shows an alternative embodiment of an improved external charger 210 with the ability to determine the position of an implanted device. In this embodiment, two or more cylindrical field sensing coils 240a-b are arranged within the primary coil 130 and wound around axes perpendicular to the central axis 275 of primary coil 130. Since the axes of the sensing coils 240a-b are perpendicular to the axis of the primary coil 130, coupling between the primary coil 130 and the sensing coils 240a-b is mitigated. The sensing coils 240a-b are therefore more likely to be affected by the magnetic fields reflected from the implant 100. When a sensing coil 240 is placed with its axis perpendicular to the direction of the magnetic field, i.e., in perfect alignment with the implanted device 100, the voltage across sensing coils 240a and 240b equals zero. With misalignment, however, the reflected magnetic field 295 contains components that are tangential to the axis of the sensing coils 240a-b, resulting in a non-zero voltage. To measure this tangential component and, by this measurement, to estimate a misalignment, it is preferred to place sensing coils 240a-b in the center of primary coil 130, with their axes lying in the primary coil 130 plane and oriented to measure misalignment in a particular axial direction. Thus, one sensing coil 240b is needed to detect the misalignment of the implant 100 in the x-direction, and another sensing coil 240a is needed to detect the misalignment of the implant 100 in the y-direction. For mechanical reasons discussed below with reference to FIG. 6C, it is helpful to divide the sensing coil 240a and 240b for each axial measurement into two separate parts and then connect the separate parts to each other using wires 244a and 244b. This way, only a single coil voltage needs be measured for each axial direction. By comparing these voltages, the position of the implant 100 can be determined. The coils may be constructed as, for example, air-core coils or ferrite-core coils. If the field sensing coils 240a-b are centered directly over implant 100, zero volts will be registered by the alignment sensing circuitry 281 (FIG. 6B) of the external charger 210. The role of insert piece 241 and cylinder holders 242 and 243 will be discussed in further detail below with regard to FIG. 6C.

Figure 6B:
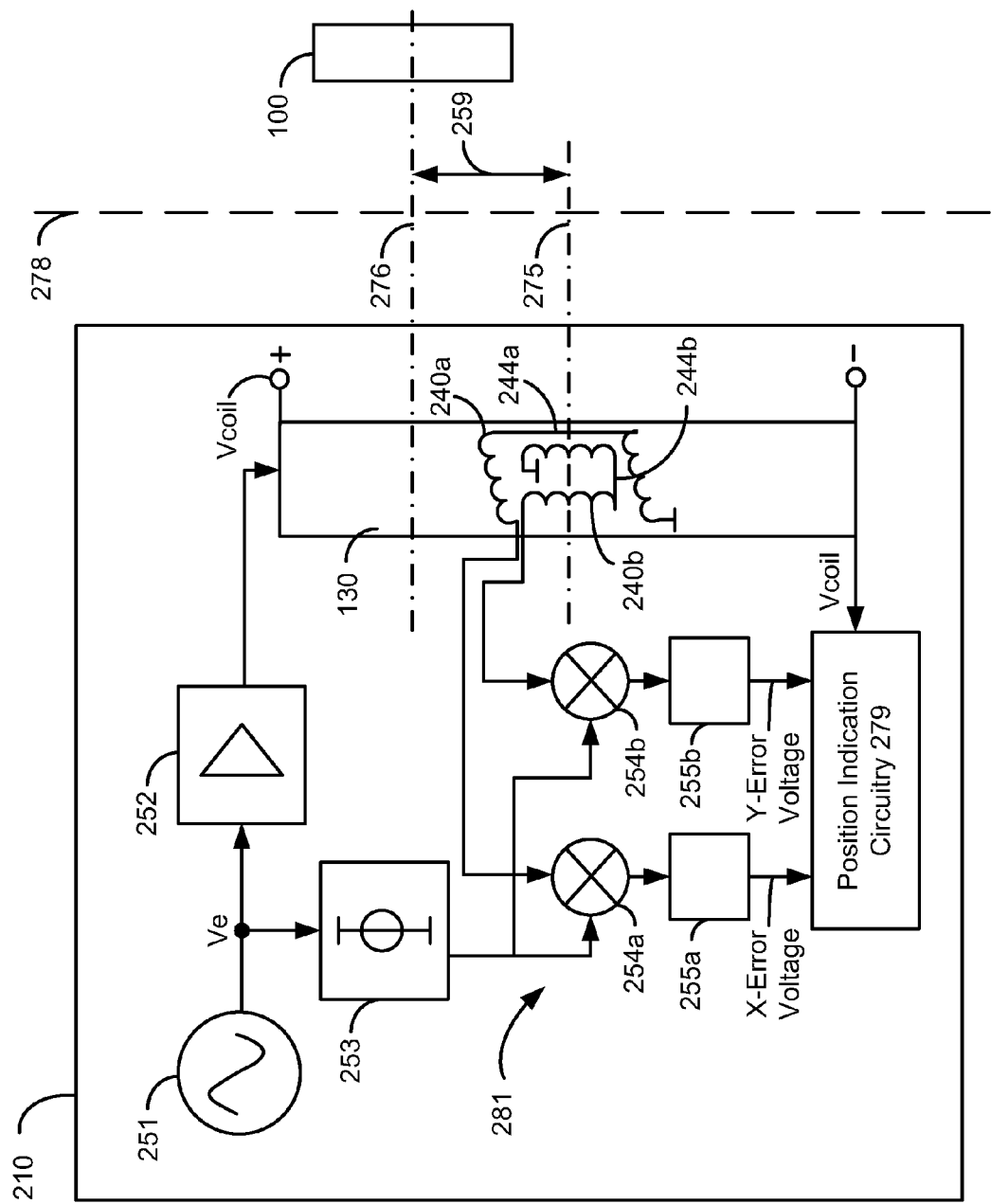
FIG. 6B shows a circuit diagram for a system comprising an improved external charger for an implantable medical device.

FIG. 6B shows a circuit diagram depicting the alignment sensing circuitry 281 of the improved external charger 210 depicted in FIG. 6A. Primary coil 130 is powered by amplifier 252, which is excited by oscillator 251. A pair of mixers 254a and 254b, which are referenced to the excitation voltage, Ve, are used to detect the direction of the magnetic flux going through field sensing coils 240a and 240b, respectively. Because the voltage across field sensing coils 240a and 240b and the excitation voltage, Ve, could be out of phase, additional phase shifter 253 is used to equalize the phases. Output from the mixers 254a and 254b are filtered by low pass filters 255a and 255b, respectively, to get an x-error voltage and a y-error voltage, the magnitudes of which represent the misalignment of the primary coil 130 and the implanted device 100. The magnitude information is sent to the external charger 210's position indication circuitry 279, wherein calculations are performed to determine the degree and direction of misalignment 259 of the implanted device 100. Indication signals for the user are then generated and sent to any of various display or indication apparatuses, as are described below. Insert piece 241 and cylinder holders 242 and 243 are not shown in FIG. 6B for simplicity.

FIG. 6C shows a top down view of one of many possible mechanical designs for the improved external charger apparatus pictured in FIGS. 6A and 6B. To detect small distortions within a strong magnetic field, field sensing coils 240a and 240b have to be precisely balanced. It may not be mechanically practical to balance the halves of the sensing coils 240a and 240b by physically moving or tilting them, although that is possible. It may instead be easier to "tilt" the magnetic field of the sensing coils 240a and 240b. An insert, 241, typically a small piece of material with high magnetic permeability such as ferrite or powdered iron, can be used for this purpose. Placing the ferrite (or other suitable material) insert 241 exactly into the geometrical center of the coil system 240 does not affect field symmetry. However, moving the insert piece 241 along the sensing coil 240a or 240b's axis changes field "tilt" for that particular sensing coil, but has no effect on the other coil. So, tilting of the magnetic fields for both the x-axis coil 240b and y-axis coil 240a can be achieved by moving insert piece 241 directionally along either axis. This can be achieved by using a rotatable insert piece holder 243. Insert piece holder 243 can be made with two concentric cylinders. The smaller cylinder 242 could be rotated inside the larger holder cylinder 243. The larger holder cylinder 243 can then be rotated inside the overall coil system. Insert piece 241 is preferably inserted into the small cylinder 242 asymmetrically, shifted to the edge of the cylinder. The small cylinder 242 is then inserted asymmetrically into the larger holder cylinder 243. By rotating the smaller cylinder 242, the displacement between the insert 241 and the coil system's main axis can be changed from zero to a maximum value. By rotating the larger holder cylinder 243, the direction of the displacement will be changed, and the sensing coils 240a and 240b may be precisely balanced so that they are able to detect small distortions in the reflected magnetic field 295.

Figure 7:
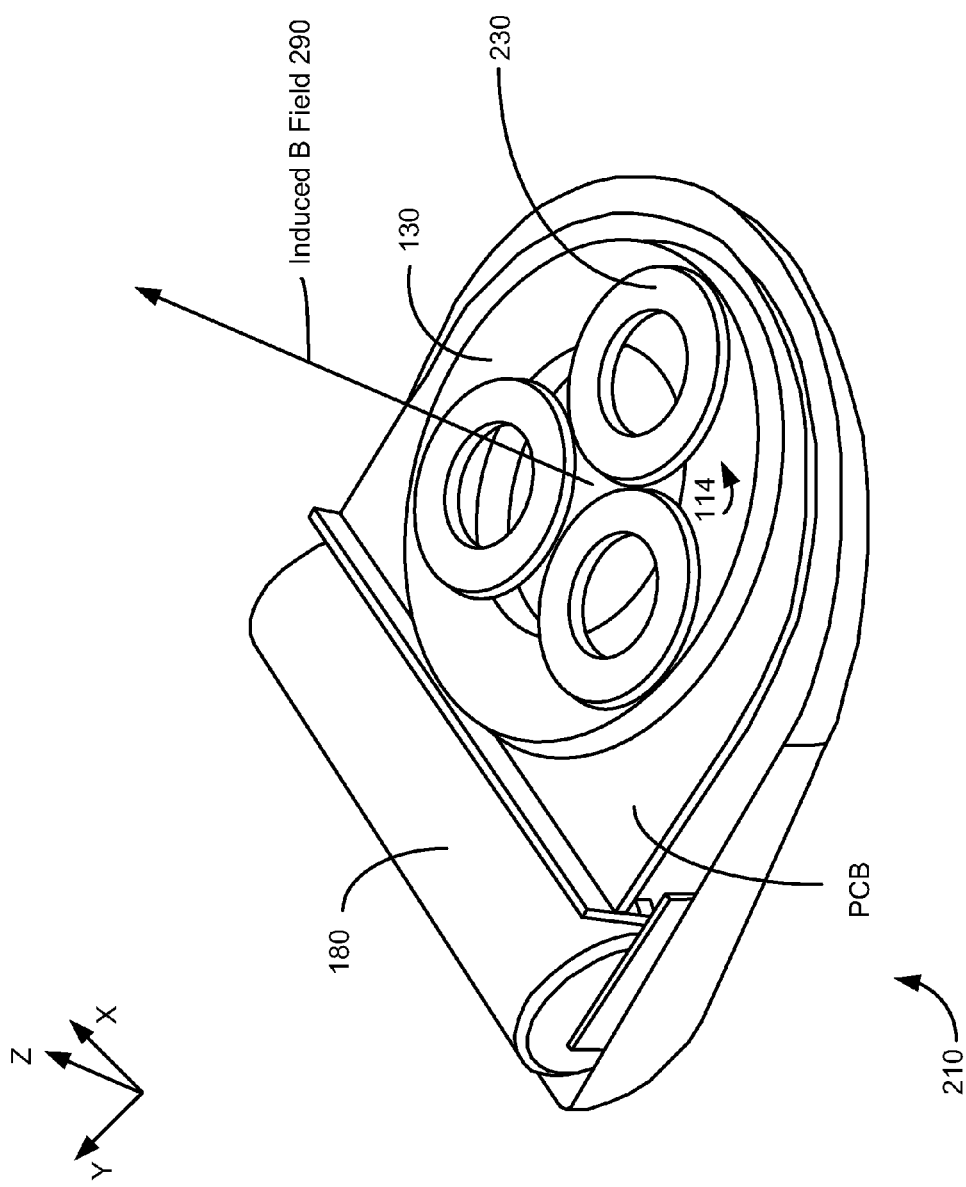
FIG. 7 shows a perspective view of one possible embodiment of an improved external charger for an implantable medical device.

FIG. 7 shows another embodiment of an improved external charger 210 with the ability to determine the relative position of an implanted device, and thus maximize coupling by indicating to the user how to improve charger/device alignment. Previous embodiments used x-y based sensors. However, position can also be "triangulated" using an embodiment with three sensing coils positioned triangularly with respect to the central axis 275 of the primary coil. In such an embodiment, three field sensing coils 230 are arranged within the primary coil 130 in a plane parallel to the primary coil 130. The field sensing coils 230 are designed to detect the amount of the reflected magnetic field 295 passing through them. The cross sectional areas of the sensing coils 230 should be maximized to increase sensitivity to the reflected magnetic field 295. The coils 230 may be constructed either as air-core coils or ferrite-core coils. By comparing the relative reflected magnetic field strengths induced in the sensing coils 230, the position of the implant can be "triangulated," i.e., determined by the external charger 210's position indication circuitry 279 (FIGS. 5C-5F). Such triangulation techniques may also be applied to the coils 240 of FIGS. 6A-6C.

Figure 1:
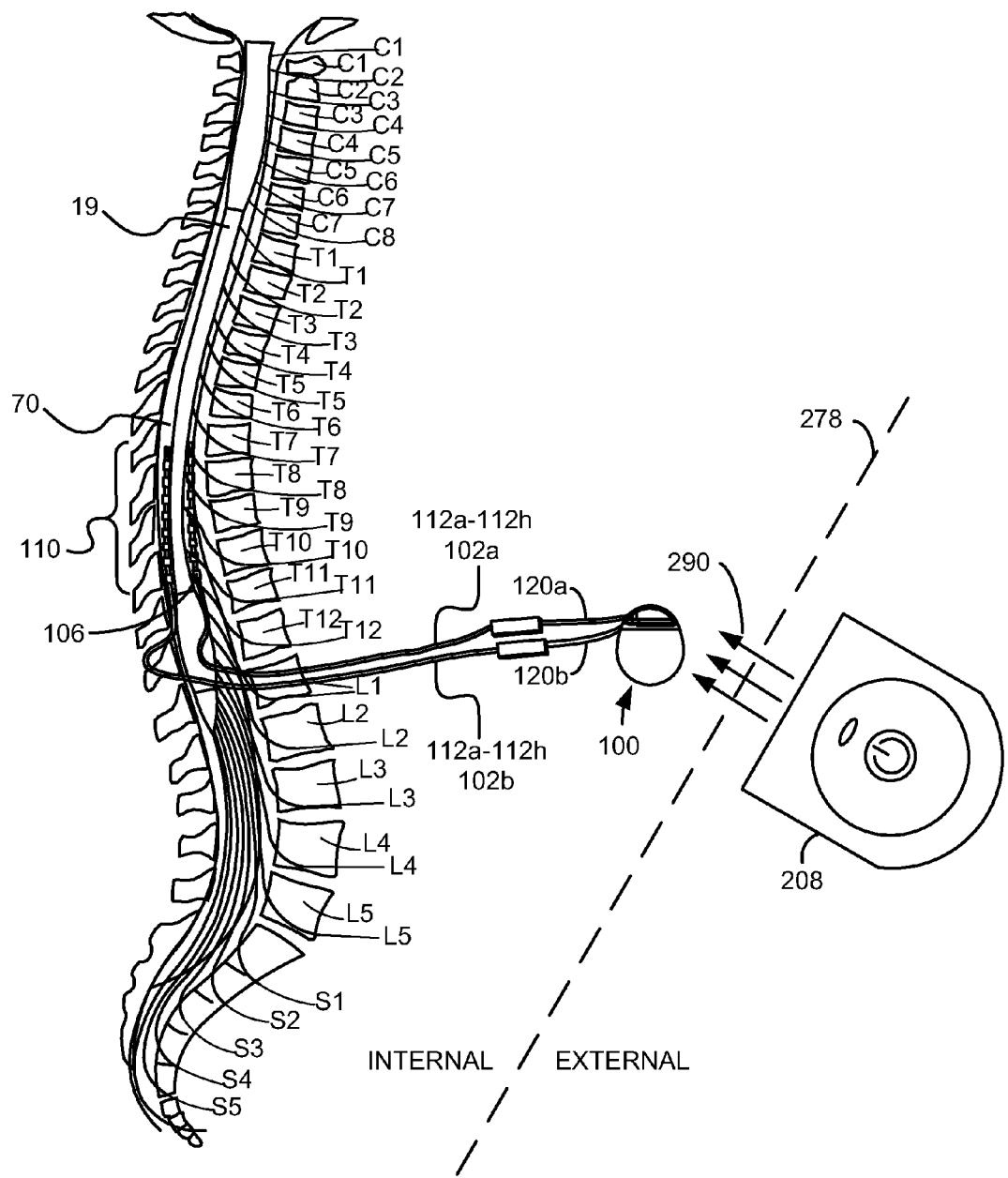
FIG. 1 shows an implantable pulse generator (IPG), an external charger, and the manner in which an electrode array is coupled to the IPG, in accordance with the prior art.
Figure 2:
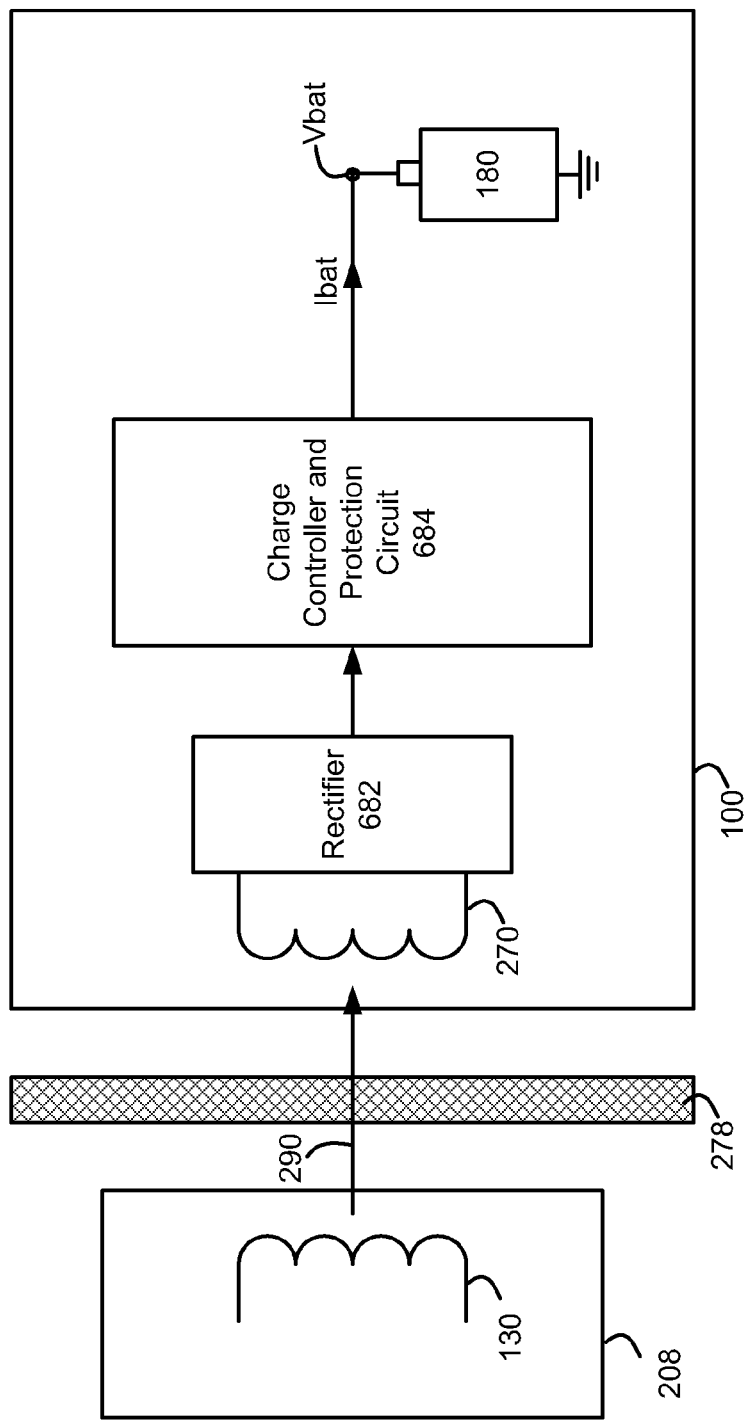
FIG. 2 illustrates a prior art system comprising an external charger for charging an implantable pulse generator, including the charge controller and battery protection aspects of the IPG.
Figure 3:
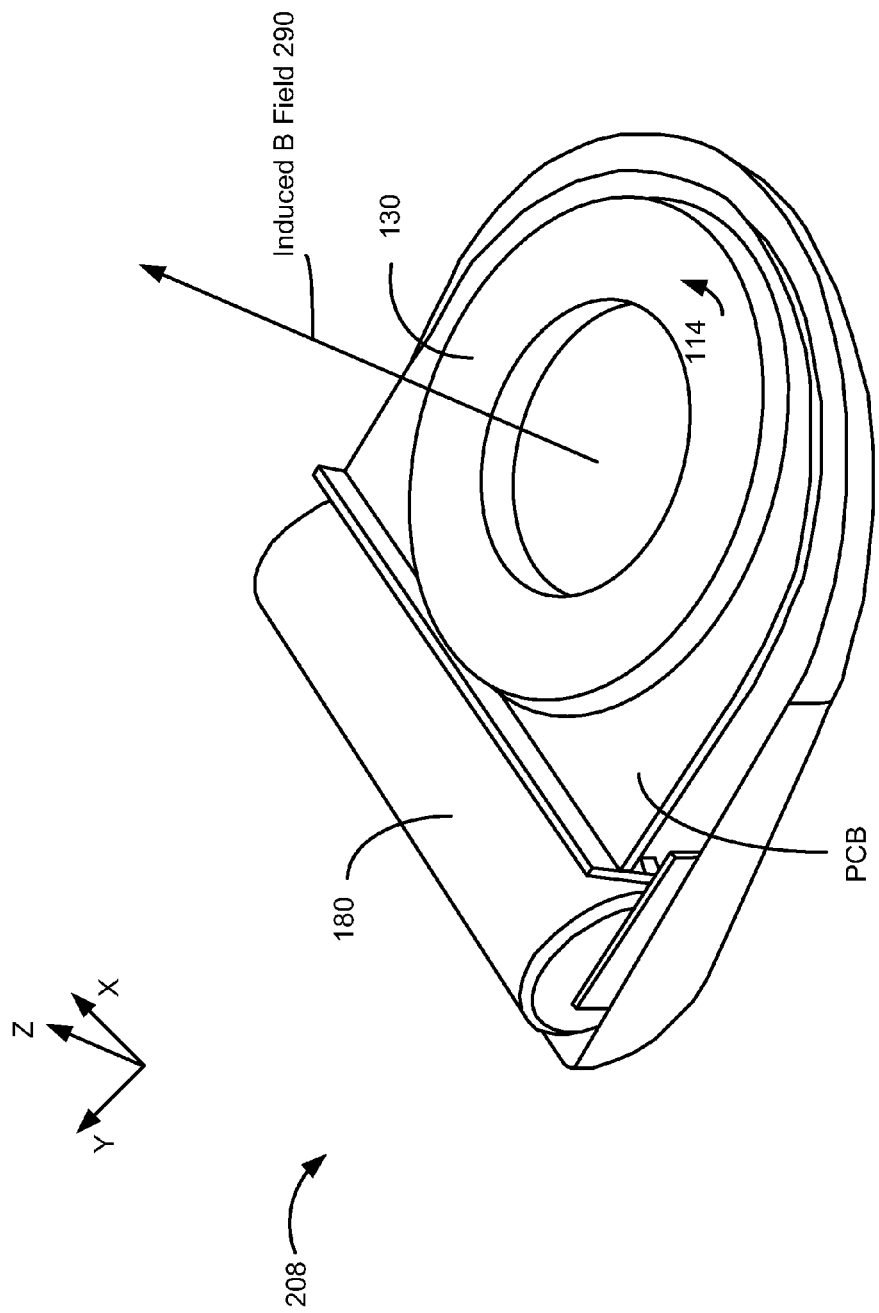
FIG. 3 shows a perspective view of a prior art external charger for an implantable medical device.
Figure 8:
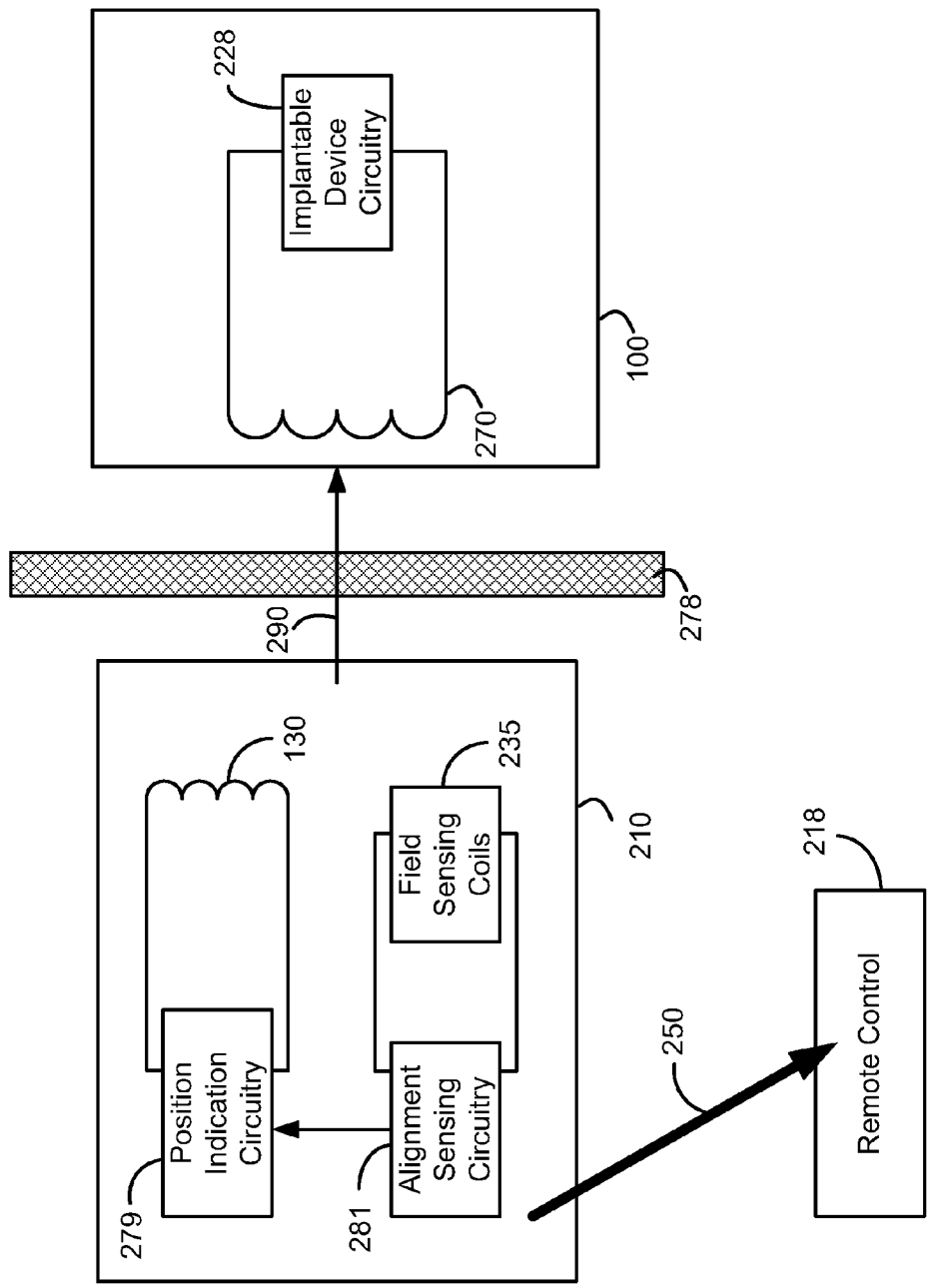
FIG. 8 shows a system comprising an improved external charger for charging an implantable pulse generator, including the alignment sensing and position indication circuitry of the external charger.

FIG. 8 shows a block diagram of an improved alignment detection system comprising an improved external charger 210 for generating a magnetic field, including the field sensing coils 235 (which could consist of either field sensing coils 230, field sensing coils 240, or other similar coils), alignment sensing circuitry 281 for measuring reflections of the magnetic field, and the position indication circuitry 279. The implantable device's circuitry 228 is similar to that described in reference to FIG. 2 above, and is shown in a block for simplicity. Alignment sensing circuitry 281 comprises the circuitry for reading the field sensing coils 235 and may be affixed to the PCB of the external charger 210, as mentioned above. Alignment sensing circuitry 281 sends the field sensing coil information to the position indication circuitry 279, which discerns the alignment between the implanted device 100 and the external charger 210. Position indication circuitry 279 then indicates to the user a direction in which the external charger 210 should be moved to improve the alignment of the external charger 210 relative to the implantable medical device 100. Such indication may occur in a variety of ways, including, but not limited to: activating visual indicators, such as LED lights 295 which can be configured to light up on the surface of the external charger 210 (See FIG. 10); activating audible indicators, such as beeps or verbal commands to the user; or activating tactile indicators, such as vibrating certain sides of the external charger 210 to indicate that the external charger 210 needs to be moved in that direction.

Because external charger 210 is often placed against a patient's back or buttocks, it can be difficult for the patient to receive information from the external charger 210 indicating how to improve the charger's alignment. To provide better positioning information to the patient, the external charger 210 may optionally transmit, via communications link 250, misalignment information to another external device for controlling the therapeutic settings of the implantable medical device, e.g., remote control 218. The external device may then indicate how the external charger 210 should be moved to improve the alignment of the external charger 210 relative to the implantable medical device 100. This type of communication is disclosed in commonly-owned U.S. Patent Application Publication 2010/0305663.

Figure 9:
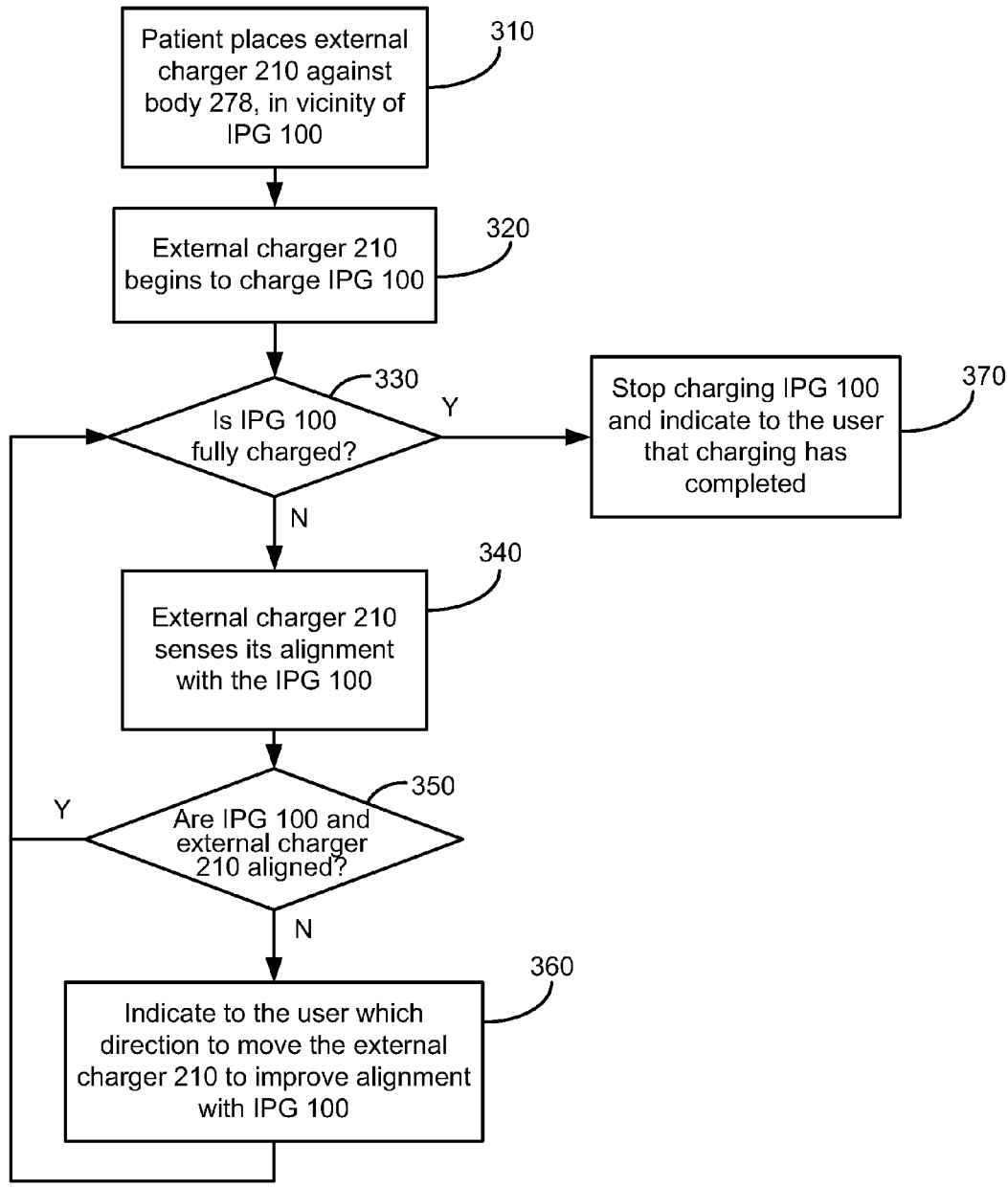
FIG. 9 is a flowchart detailing one embodiment of a technique for assuring the proper alignment of an external charger to an IPG.

FIG. 9 is a flowchart detailing one embodiment of a technique for assuring the proper alignment of an external charger 210 to an IPG 100. First, the user places external charger 210 against the surface of his body 278 in the known vicinity of IPG 100 (310). At this time, the patient will activate the external charger 210 and begin charging IPG 100 (320). The default setting for external charger 210 is maximum power output. As long as external charger doesn't receive an indication that IPG 100 is fully charged (330), it will continue to charge IPG 100. As external charger 210 is charging IPG 100, alignment sensing circuitry 281 in the external charger 210 senses the charger's alignment with the IPG 100 based at least in part on electrical measurements taken from the plurality of sensing coils 235 in the external charger 210, and position indication circuitry 279 calculates the IPG 100's location (340). This calculation occurs in real time (340) so that, any time alignment becomes poor, corrective action can be indicated to the user and taken in subsequent steps. If IPG 100 and the external charger 210 are properly aligned (350), external charger 210 continues to charge the IPG 100's internal power source 180 until receiving indication that IPG 100 is fully charged (330). If the external charger 210 determines that IPG 100 and the external charger 210 are not properly aligned (350), the external charger 210 will indicate to the user (via one of the various methods discussed above) which direction to move the external charger 210 to improve alignment (360) while still continuing to charge IPG 100. Once the external charger 210 determines that the IPG 100's internal power source 180 is fully charged (330), it will indicate via an audible beep or other visual indication to the user that the charging process has completed (370).

Figure 10:
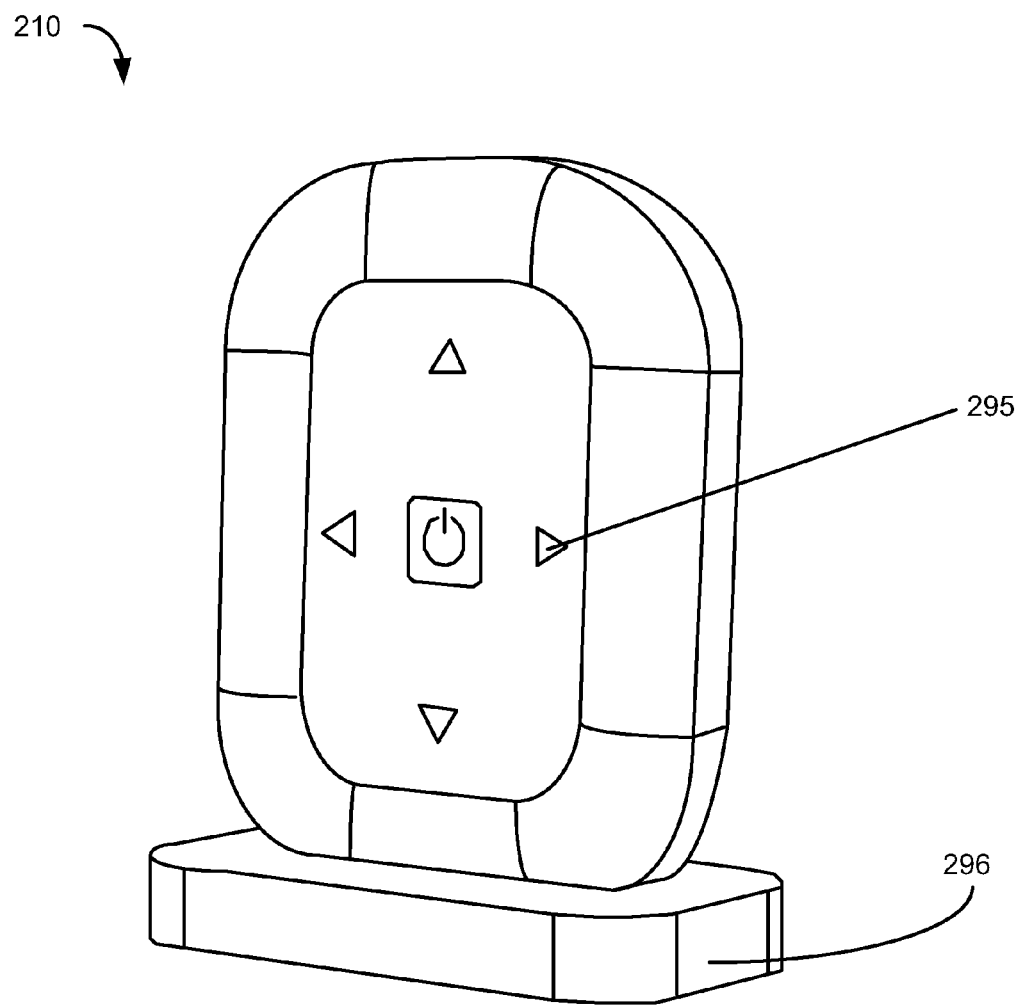
FIG. 10 shows one embodiment of an improved external charger for charging an implantable pulse generator.

FIG. 10 shows one embodiment of an improved external charger 210 for charging an implantable device. The external charger 210 is shown sitting in a base unit 296. In this embodiment, four arrow-shaped LED lights 295 are arranged on the surface of the external charger 210, with one arrow-shaped LED light pointing towards each edge of external charger 210. As position indication circuitry 279 determines in which direction the external charger 210 should be moved to provide better alignment with implantable device 100, it can send an appropriate control signal to illuminate one or more of the LED lights 295 to indicate that direction to the user. When position determination circuitry 279 has detected that there is a satisfactory degree of alignment between the external charger 210's primary coil 130 and the implantable device, position indication circuitry 279 will send a control signal to turn off each LED light 295 until it again senses a misalignment condition during charging.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An external charger for use with an implantable medical device, comprising:
a primary coil for producing a magnetic field for providing power to an implantable medical device;
a plurality of sensing coils for sensing reflections of the magnetic field from the implantable medical device; and
an alignment sensing circuit for determining an alignment of the primary coil relative to the implantable medical device, wherein the determination is based on electrical measurements taken from the plurality of sensing coils in response to the sensed reflections.

2. The external charger of claim 1, further comprising:
a position indication circuit coupled to the alignment sensing circuit for indicating to a user a misalignment of the external charger relative to the implantable medical device.

3. The external charger of claim 2, wherein the indication circuit further indicates to the user how to improve the alignment of the external charger relative to the implantable medical device.

4. The external charger of claim 2, wherein the indication circuit activates visual indicators on the external charger.

5. The external charger of claim 4, wherein the visual indicators indicate a direction in which the external charger should be moved to improve the alignment of the external charger relative to the implantable medical device.

6. The external charger of claim 2, wherein the position indication circuit transmits misalignment information to another external device.

7. The external charger of claim 6, wherein the another external device indicates how the external charger should be moved to improve the alignment of the external charger relative to the implantable medical device.

8. The external charger of claim 1, wherein the electrical measurement comprises a voltage across at least one of the plurality of sensing coils.

9. The external charger of claim 1, wherein the plurality of sensing coils are located within a center of the primary coil.

10. The external charger of claim 1, wherein the primary coil is wound around a central axis, and wherein the plurality of sensing coils are wound around axes that are parallel to the central axis.

11. The external charger of claim 1, wherein the primary coil is wound around a central axis, and wherein the plurality of sensing coils are wound around second axes, and wherein the second axes are perpendicular to the central axis.

12. The external charger of claim 1, wherein the plurality of sensing coils comprises at least one pair of sensing coils, wherein the coils in each pair straddle a central axis of the primary coil.

13. The external charger of claim 12, wherein the coils in each pair are wound around axes that are parallel to the central axis of the primary coil.

14. The external charger of claim 12, wherein the coils in each pair are wound around axes that are perpendicular to the central axis of the primary coil.

15. The external charger of claim 12, wherein the coils in each pair are connected to each other.

16. The external charger of claim 15, wherein the coils in each pair are connected in series and end-to-end.

17. The external charger of claim 12, wherein the coils in each pair are not connected to each other.

18. The external charger of claim 12, comprising two pairs of sensing coils positioned orthogonally with respect to each other.

19. The external charger of claim 12, comprising three sensing coils positioned triangularly with respect to the central axis of the primary coil.

\* \* \* \* \*

UNITED STATES PATENT AND TRADEMARK OFFICE
CERTIFICATE OF CORRECTION

PATENT NO. : 8,473,066 B2
APPLICATION NO. : 12/498049
DATED : June 25, 2013
INVENTOR(S) : Daniel Aghassian et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 569 days.

Signed and Sealed this
Ninth Day of December, 2014

Michelle K. Lee
*Deputy Director of the United States Patent and Trademark Office*